US006872838B2

(12) United States Patent
Stella et al.

(10) Patent No.: US 6,872,838 B2
(45) Date of Patent: Mar. 29, 2005

(54) WATER SOLUBLE PRODRUGS OF HINDERED ALCOHOLS

(75) Inventors: Valentino J. Stella, Lawrence, KS (US); Jan J. Zygmunt, Longmont, CO (US); Ingrid Gunda Georg, Lawrence, KS (US); Muhammad S. Safadi, Nazareth (IL)

(73) Assignee: University of Kansas, Lawrence, KS (US)

( * ) Notice: Subject to any disclaimer, the term of this patent is extended or adjusted under 35 U.S.C. 154(b) by 0 days.

(21) Appl. No.: 10/208,647

(22) Filed: Jul. 29, 2002

(65) Prior Publication Data

US 2003/0176324 A1 Sep. 18, 2003

Related U.S. Application Data

(62) Division of application No. 09/733,817, filed on Dec. 8, 2000, now Pat. No. 6,451,776, which is a division of application No. 09/131,385, filed on Aug. 7, 1998, now Pat. No. 6,204,257.

(51) Int. Cl.[7] .......................... C07D 493/02; C07F 9/06
(52) U.S. Cl. ....................... 549/220; 558/187; 558/177; 549/298; 549/408
(58) Field of Search .................................. 549/220, 298, 549/408; 558/187, 177; 546/23; 562/15

(56) References Cited

U.S. PATENT DOCUMENTS

| | | |
|---|---|---|
| 2,829,151 A | 4/1958 | Britton et al. |
| 3,271,314 A | 9/1966 | Ecke et al. |
| 3,576,923 A | 4/1971 | Randell et al. |
| 3,723,578 A | 3/1973 | Eiseman et al. |
| 4,171,272 A | 10/1979 | Wright |
| 4,894,456 A | 1/1990 | Wall et al. |
| 4,912,245 A | 3/1990 | Girardeau et al. |
| 4,981,968 A | 1/1991 | Wall et al. |
| 5,039,343 A | 8/1991 | Umeda et al. |
| 5,049,668 A | 9/1991 | Wall et al. |
| 5,053,512 A | 10/1991 | Wani et al. |
| 5,091,211 A | 2/1992 | Richard |
| 5,106,742 A | 4/1992 | Wall et al. |
| 5,120,464 A | 6/1992 | Kamegai et al. |
| 5,122,526 A | 6/1992 | Wall et al. |
| 5,122,606 A | 6/1992 | Wani et al. |
| 5,180,722 A | 1/1993 | Wall et al. |
| 5,244,903 A | 9/1993 | Wall et al. |
| 5,364,858 A | 11/1994 | Wall et al. |
| 5,401,747 A | 3/1995 | Wall et al. |
| 5,554,576 A | 9/1996 | Mookerjee et al. |
| 5,589,598 A | 12/1996 | Paiocchi |
| 5,637,625 A | 6/1997 | Haynes |
| 5,646,159 A | 7/1997 | Wall et al. |
| 5,646,176 A | 7/1997 | Golik et al. |
| 5,731,355 A | 3/1998 | Jones et al. |
| 5,746,973 A | 5/1998 | Naraghi |
| 5,804,682 A | 9/1998 | Fischer et al. |
| 6,204,257 B1 * | 3/2001 | Stella et al. ................. 514/130 |
| 6,451,776 B2 * | 9/2002 | Stella et al. .................. 514/81 |

FOREIGN PATENT DOCUMENTS

| | | |
|---|---|---|
| EP | 60491 0 A1 | 7/1994 |
| EP | 604910 A1 | 7/1994 |
| EP | 0604910 A1 | 7/1994 |
| EP | 639577 A1 | 2/1995 |
| EP | 747385 A1 | 12/1996 |

OTHER PUBLICATIONS

Bioorganic & Medicinal Chemistry Letters, 6(15), Aug. 6, 1996, pp. 1837–1842 Golik et al "Synthesis and antitumor evaulation of paclitaxel . . . ".
Pharmaceutical Research, 10(9), Sep. 1993, pp. 1350–1355 Safadi et al "Phosphoryloxymethyl carbamates and carbonates . . . ".
Abstract/Japanese Kokai Tokkyo Koho patent JP–11181293 Jul. 6, 1999.
Abstract/PCT Int. Appl. WO–9929640 Jun. 17, 1999.
Abstract/PCT Int. Appl. WO–9915609 Apr. 1, 1999.
Abstract/Japanese Kokai Tokkyo Koho patent JP–10298450 Nov. 10, 1998.
Abstract/U.S. Pat. No. 5,804,682 Sep. 8, 1998.
Abstract/Japanese Kokai Tokkyo Koho patent JP–10182981 Jul. 7, 1998.
Abstract/U.S. Pat. No. 5,746,973 May 5, 1998.
Abstract/Japanese Kokai Tokkyo Koho JP–10037072 Feb. 10, 1998.
Abstract/U.S. Pat. No. 5,723,538 Mar. 3, 1998.
Abstract/Japanese Kokai Tokkyo Koho JP–09188968 Jul. 22, 1997.
Abstract/Japanese Kokai Tokkyo Koho JP–09099441 Apr. 15, 1997.
Abstract/U.S. Pat. No. 5,611,992 Mar. 18, 1997.
Abstract/U.S. Pat. No. 5,611,991 Mar. 18, 1997.
Abstract/PCT Int. Appl. WO–9628603 Sep. 19, 1996.
Abstract/Japanese Kokai Tokkyo Koho JP–08011437 Jan. 16, 1994.
Abstract/German patent DE–4426134 Jan. 25, 1996.
Abstract/Czech patent CS–277269 Dec. 16, 1992.
Abstract/Japan Kokai Tokkyo Koho JP–05222068 Aug. 31, 1993.
Abstract/Japanese Kokai Tokkyo Koho JP–05051899 Mar. 2, 1993.
Abstract/Japanese Kokai Tokkyo Koho JP–04325600 Nov. 13, 1992.
Abstract/Japanese Kokai Tokkyo Koho JP–04282390 Oct. 7, 1992.

(Continued)

Primary Examiner—Charanjit S. Aulakh
(74) Attorney, Agent, or Firm—Birch, Stewart, Kolasch & Birch, LLP

(57) ABSTRACT

The present invention is directed to novel water-soluble prodrugs of aliphatic or aromatic hindered hydroxyl group containing pharmaceuticals.

2 Claims, 4 Drawing Sheets

OTHER PUBLICATIONS

Abstract/Japanese Kokai Tokkyo Koho JP–04134088 May 7, 1992.
Abstract/Japanese Kokai Tokkyo Koho JP–04221390 Aug. 11, 1992.
Abstract/U.S. Pat. No. 5,110,503 May 5, 1992.
Abstract/Japanese Kokai Tokkyo Koho JP–04069389 Mar. 4, 1992.
Abstract/PCT Int. Appl. WO–9206596 Apr. 30, 1992.
Abstract/Japanese Kokai Tokkyo Koho JP–04055401 Feb. 24, 1992.
Abstract/Japanese Kokai Tokkyo Koho JP–04049223 Feb. 18, 1992.
Abstract/Japanese Kokai Tokkyo Koho JP–04041798 Feb. 12, 1992.
Abstract/U.S. Pat. No. 5,091,211 Feb. 25, 1992.
Abstract/Japanese Kokai Tokkyo Koho JP–03155987 Jul. 3, 1991.
Abstract/Japanese Kokai Tokkyo Koho JP–03197403 Aug. 28, 1991.
Abstract/Japanese Kokai Tokkyo Koho JP–03178904 Aug. 2, 1991.
Abstract/Eur. Pat. Appl. EP–393579 Oct. 24, 1990.
Abstract/German patent DE–3900941 Jul. 19, 1990.
Abstract/Eur. Pat. Appl. EP–365413 Apr. 25, 1990.
Abstract/Eur. Pat. Appl. EP–324451 Jul. 19, 1989.
Abstract/Japanese Kokai Tokkyo Koho JP–63185916 Aug. 1, 1988.
Abstract/Japanese Kokai Tokkyo Koho JP–63165477 Jul. 8, 1988.
Abstract/Japanese Kokai Tokkyo Koch JP–63156710 Jun. 29, 1988.
Abstract/Patentschrift (Switz.) CH–664577 Mar. 15, 1988.
Abstract/Eur. Pat. Appl. EP–252824 Jan. 13, 1988.
Ph.D. Dissertation of S. Varia, University of Kansas, May 26, 1981 "Water Soluble Prodrugs of 5,5–Diphenylhydantoin".
S.Sawada et al., "Synthesis and Antitumor Activity of A–Ring or E. Lactone Modified Water–Soluble Prodrugs of 20(S)–Camptothecin, Including Development of Irinotecan Hydrochloride Tribydrate (CPT–11)," Current Pharamceutical Design vol. 1 No. 1(1995), pp. 113–132.

* cited by examiner

WATER SOLUBLE PRODRUGS OF HINDERED ALCOHOLS

This application is a divisional of application 09/733,817 filed Dec. 8, 2000, now U.S. Pat. No. 6,451,776 which is a divisional of application 09/131,385 filed Aug. 7, 1998, now U.S. Pat. No. 6,204,257.

BACKGROUND OF THE INVENTION

1. Field of the Invention

The present invention relates to novel water-soluble prodrugs of aliphatic or aromatic hindered hydroxyl group containing pharmaceuticals. Particularly, the present invention concerns novel water-soluble phosphonooxymethyl ethers of hindered alcohol and phenol containing pharmaceuticals, such as camptothecin, propofol, etoposide, Vitamin E and Cyclosporin A. The present invention also relates to intermediates used to create the final prodrugs as well as pharmaceutical compositions containing the novel compounds.

2. Background Art

The successful delivery of a pharmaceutical to a patient is of critical importance in the treatment of disorders. However, the use of many clinical drugs with known properties is limited by their very low water solubility. As a result of low water solubility these drugs must be formulated in co-solvent pharmaceutical vehicles, including surfactants. These surfactants have been shown to lead to severe side effects in humans that limit the clinical safety of these drugs and therefore the treatment of several disorders.

For example, camptothecin is a natural product isolated from barks of the Chinese camptotheca tree, *Camptotheca accuminata*. It has been shown to have strong anti-tumor activity in several in vivo animal models including major tumor types such as lung, breast, ovary, pancreas, colon and stomach cancer and malignant melanoma. Camptothecin inhibits the cellular enzyme DNA topoisomerase I and triggers a cascade of events leading to apoptosis and programmed cell death. Topoisomerase I is essential nuclear enzyme responsible for the organization and modulation of the topological feature of DNA so that a cell may replicate, transcribe and repair genetic information.

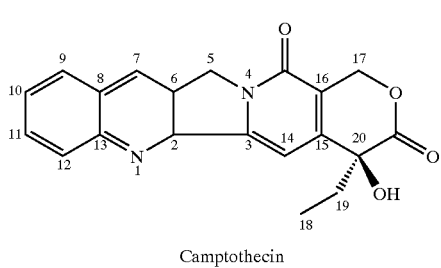

Camptothecin

Figure 1

The serious drawback of camptothecin is its very limited water solubility. For biological studies it is necessary to dissolve the compound in a strong organic solvent (DMSO) or to formulate the drug as a suspension in Tween 80:saline which is an undesirable drug formulation for human therapy. Recently two analogs of camptothecin with moderate water solubility have been approved in United States for treatment of advanced ovarian cancer (Hycamtin) and colorectal cancer (Camptosar).

Other drugs, like camptothecin, that have similar problems are cyclosporin A (CsA), propofol, etoposide and Vitamin E (alpha-tocopherol). Like camptothecin, CsA has within its structure a sterically hindered alcohol, a secondary alcohol in this case. CsA is formulated in a CremophorEL/ethanol mixture.

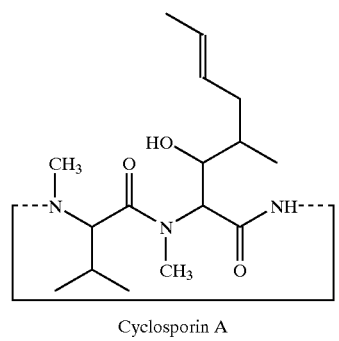

Cyclosporin A

An example of a sterically hindered, poorly water soluble phenol is propofol, an anesthetic.

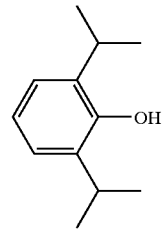

Proforol (2,6-diisopropylphenol)

Propofol is formulated for i.v. clinical use as a o/w emulsion. Not only is propofol poorly water soluble, but it also causes pain at the site of injection. This pain must be ameliorated by using lidocaine. Due to the fact that it is formulated as an emulsion, it is difficult and questionable to add other drugs to the formulation and physical changes to the formulation such as an increase in oil droplet size can lead to lung embolisms, etc. A water soluble and chemically stable prodrug of propofol would provide several advantages. Such a formulation could be a simple aqueous solution that could be admixed with other drugs. If the prodrug itself was painless, the prodrug may be more patient friendly, and finally there should be no toxicity due to the vehicle. Other poorly water soluble, sterically hindered phenols are the anticancer drug, etoposide and Vitamin E (alpha-tocopherol).

The present invention provides a water soluble form of alcohol and phenol containing drugs such as camptothecin and propofol. With respect to camptothecin, compounds according to the present inventions are phosphonooxymethyl ethers of camptothecin in the form of the free acid and pharmaceutically acceptable salts thereof. The water solubility of the acid and the salts facilitates preparation of pharmaceutical formulations. All of the prodrugs according to the present invention exhibit superior water solubility compared to their respective parent drugs. The methods developed for the compounds of the present invention can be useful for conversion of many other water insoluble medicinal agents having aliphatic or aromatic hindered hydroxyl groups to the water soluble derivatives.

SUMMARY OF THE INVENTION

The invention described herein involves new compositions of matter. The invention relates to the water soluble phosphonooxymethyl derivatives of alcohol and phenol containing pharmaceuticals represented by the general formula I:

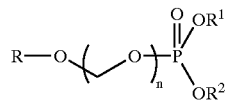

The above formula I is the derivative of ROH, wherein ROH represents an alcohol- or phenol-containing drug, such as camptothecin, propofol, etoposide, vitamin E and cyclosporin A. In the above formula I, n represents an integer of 1 or 2. When n is 2, ROH is preferably a phenol-containing pharmaceutical, such as propofol. Also included are some drugs for which injectable forms are not possible due to their inherent poor water solubility. These include danazol, methyltestosterone, iodoquinol and atovaquone. $R^1$ is hydrogen or an alkali metal ion including sodium, potassium or lithium or a protonated amine or protonated amino acid or any other pharmaceutically acceptable cation. $R^2$ is hydrogen or an alkali metal ion including sodium, potassium or lithium or a protonated amine or a protonated amino acid or any other pharmaceutically acceptable cation. After intravenous or oral administration, the derivatives according to formula I are converted back to the parent drugs by hydrolysis and/or phosphatase.

Accordingly, it is an object of the present invention to develop derivatives of water insoluble drugs which exhibit good activity and water solubility.

It is another object of the present invention to develop pharmaceutical compositions of these water soluble compounds, which comprises an amount of the compound of formula I and a pharmaceutically acceptable carrier.

It is another object of the present invention to develop drug derivatives having good stability at pH levels suitable for making pharmaceutical formulations, but quickly break down in vivo under physiological conditions, to potentially act as prodrugs.

BRIEF DESCRIPTION OF THE DRAWINGS

The drawings of the present application are explained as follows.

DETAILED DESCRIPTION OF THE INVENTION

Figure 1:
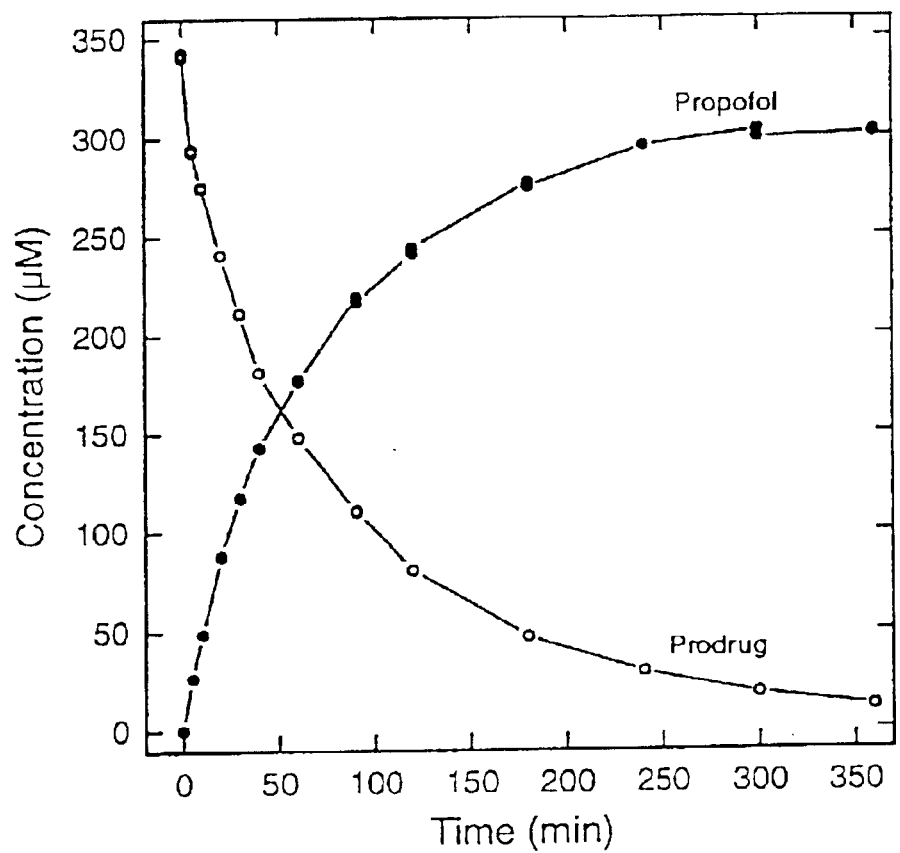
FIG. 1 illustrates an in vitro enzymatic conversion of propofol prodrug to propofol.

In the present specification, unless otherwise specified or in context, the following definitions apply.

"Phosphono-" means the group —P(O)(OH)2 and "phosphonooxymethoxy" or "phosphonooxymethyl ether" means generically the group —OCH$_2$OP(O)(OH)$_2$. "Methylthiomethyl" refers to the group —CH$_2$SCH$_3$. The present invention also encompasses compounds wherein n=2 such that a "phosphono-di(oxymethyl) ether" generically means the group —OCH$_2$OCH$_2$OP(O)(OH)$_2$.

"Camptothecin moiety" denotes moiety containing the twenty carbon camptothecin core framework including two nitrogen atoms and four oxygen atoms as represented by the structural formula shown below with the absolute configuration.

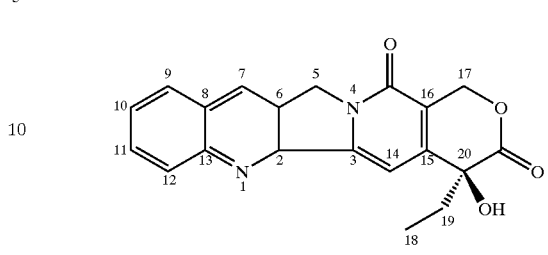

The numbering system shown above is one used in conventional camptothecin derivatives, and is followed throughout the application. For example the notation C20 refers to the carbon atom labeled as "20".

"Camptothecin analogue" refers to a compound having the basic camptothecin core framework. It is to be understood that camptothecin analogues encompass compounds including but not limited to the following compounds: Topotecan, available from SmithKline Beecham, Irinotecan (CPT-11), available from Pharmacia & Upjohn, 9-Aminocamptothecin (9AC), 9-Nitrocamptothecin (9NC), GI 147211C, available from Glaxo Wellcome, and DX-8951f (the previous six camptothecin anologues are currently under clinical investigation and are described in a review conducted by the Pacific West Cancer Fund authored by Claire McDonald (December 1997).

Additionally, several other non-limiting Camptothecin analogues which are herein incorporated by reference are disclosed by Sawada et al., *Current Pharmaceutical Design*, Vol. 1, No. 1, pp 113–132, as well as U.S. Pat. Nos. 5,646,159, 5,559,235, 5,401,747, 5,364,858, 5,342,947, 5,244,903, 5,180,722, 5,122,606, 5,122,526, 5,106,742, 5,053,512, 5,049,668, 4,981,968 and 4,894,456.

Several pharmaceutical compounds including their respective derivatives of camptothecin contain more than one hydroxyl group, for example 10-hydroxycamptothecin, topotecan and several others listed in the above references. It is herein understood that the present invention may be applied to more than one hydroxyl group. This may be accomplished by protecting the additional hydroxyl group prior to derivatization.

"Phosphono protecting groups" means moieties, which can by employed to block or protect the phosphono functional group. Preferably, such protecting groups are those that can be removed by methods that do not appreciably affect the rest of the molecule. Suitable phosphonooxy protecting groups include for example benzyl (denoted by "Bn"), t-butyl, and allyl groups.

"Pharmaceutically acceptable salt" means a metal or an amine salt of the acidic phosphono group in which the cation does not contribute significantly to the toxicity or biological activity of the active compound. Suitable metal salts include lithium, potassium, sodium, calcium, barium, magnesium, zinc, and aluminum salts. Preferred salts are sodium and potassium salts. Suitable amines salts are for example, ammonia, tromethamine, triethanolamine, ethylenediamine, glucamine, N-methylglucamine, glycine, lysine, ornithine, arginine, ethanolamine, to name but a few. Preferred amine salts are lysine, arginine, N-methylglucamine, and tromethamine salts.

In the specification and in the claims, the term —OCH$_2$OP(O)(OH)$_2$ is intended to encompass both the free acid and its pharmaceutically acceptable salts, unless the context indicates specifically that the free acid is intended.

One aspect of the present invention provides for derivatives of alcohol and phenol containing pharmaceuticals as shown in formula I:

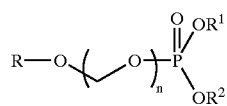

The derivatives according to formula I can be prepared according to the reaction sequence shown in Scheme 1:

Scheme 1

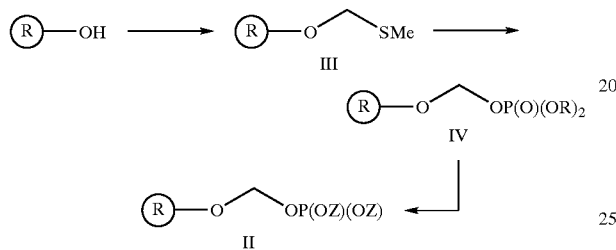

wherein ROH represents an alcohol- or phenol-containing drug, such as camptothecin, propofol, etoposide, vitamin E, cyclosporin A. It is to be understood that the above pathway is just one of several alternate pathways. These alternate pathways will become evident upon review of the following disclosure and examples.

An example of the above Scheme 1 can be illustrated using the compound camptothecin. It is to be understood that these schemes are applicable to other compounds encompassed by formula I of the present invention, such as those listed above. Accordingly, another aspect of the present invention provides camptothecin derivatives of according to formula II:

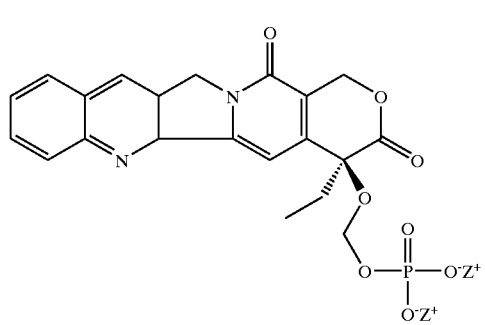

which include the free acid wherein Z is hydrogen and pharmaceutically acceptable salts thereof wherein Z is metal or amine. Alternatively, formula II includes diacids where Z is metal or amine in both occurrences.

The preferred pharmaceutically acceptable salts of a compound of formula II are alkali salts including lithium, sodium, and potassium salts; and amine salts including triethylamine, triethanolamine, ethanolamine, arginine, lysine and N-methylglucamine salts.

The most preferred embodiments of camptothecin derivatives of formula II include the following compounds: (20)-O-phosphonooxymethylcamptothecin, (20)-O-phosphonooxymethylcamptothecin mono- or di-sodium salt, (20)-O-phosphonooxymethylcamptothecin mono or di-potassium salt, (20)-O-phosphonooxymethyl-camptothecin mono- or di-arginine salt, (20)-O-phosphonooxymethylcamptothecin mono- or di-lysine salt, (20)-O-phosphonooxymethylcamptothecin mono- or di-N-methylglucamine salt and (20)-O-phosphonooxymethyl-camptothecin mono- or di-triethanolamine salt.

Compounds of formula II may be prepared directly from camptothecin (shown as ©-OH) according to the reaction sequence shown in Scheme 2:

Scheme 2

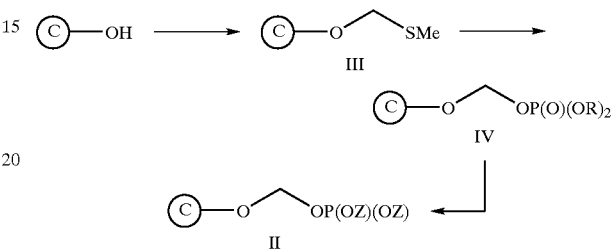

A compound of formula III (methylthiomethyl ether, MTM ether) may be prepared by treating camptothecin with dimethylsulfoxide/acetic anhydride/acetic acid.

In the second step shown in Scheme 2, the methylthiomethyl ether is converted to the corresponding protected phosphonooxymethyl ether (compound of formula IV). This is accomplished by treating the MTM ether with N-iodosuccinamide and protected phosphate HOP(O)(OR)$_2$. In the third step, the phosphono protecting groups are removed to provide a compound of formula II. For example, a suitable phosphono protecting group(s) is benzyl that may be removed by catalytic hydrogenolysis.

The general process of Scheme 2 for the preparation of a compound of formula I is more particularly exemplified in Scheme 3:

Scheme 3

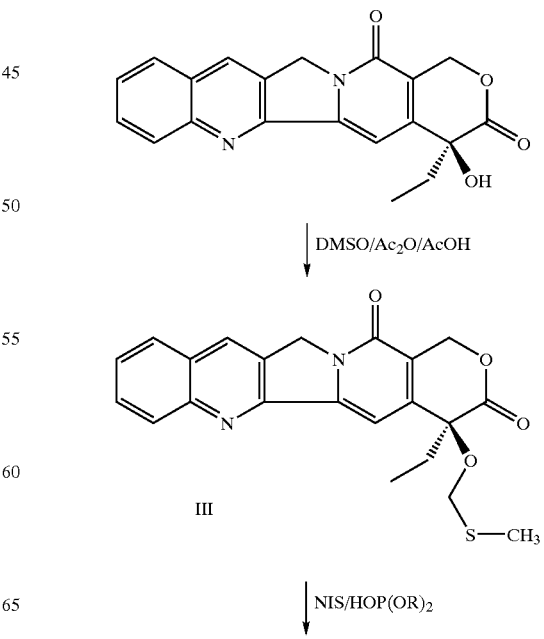

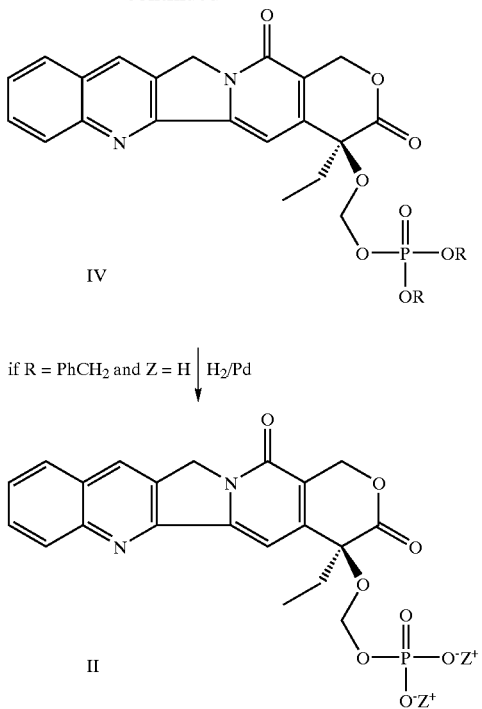

In the first step, the free hydroxy group of the camptothecin is converted to the corresponding methylthiomethyl ether (—OCH$_2$SCH$_3$) group. This conversion may be accomplished by reaction with dimethylsulfoxide in the presence of acetic anhydride and acetic acid. This method, commonly known as the Pummer reaction was successfully applied by Bristol-Myers Squibb for methylthiomethylation of taxol (Europ.Pat.0604910A1, Bioorg.Med.Chem.Lett.,6, 1837,1996). The reaction is usually carried out at room temperature, and for 24–72 hours to produce the methylthiomethyl ether.

In the second step of the reaction sequence, the methylthiomethyl ether is converted to the corresponding protected phosphonooxymethyl ether. This well-known conversion was successfully applied by Bristol-Myers Squibb for phosphonooxymethylation of taxol (Europ.Pat.0604910A1, Bioorg.Med.Chem.Lett.,6,1837,1996). Thus, a compound of formula III is treated with N-iodosuccinamide and protected phosphoric acid such as dibenzyl phosphate. The reaction is carried out in an inert organic solvent such as tetrahydrofuran and halogenated hydrocarbon such as methylene chloride and in the presence of molecular sieves. Reaction is carried out at room temperature. N-iodosuccinimide and protected phosphoric acid are used in excess (3–5 equivalents) relative to the methylthiomethyl ether.

In the third step of the reaction sequence, the phosphono protecting groups are removed. The deblocking is accomplished by conventional methods well known in the art such as acid- or base-catalyzed hydrolysis, hydrogenolysis, reduction, and the like. For example, catalytic hydrogenolysis can be used to remove the benzyl phosphono-protecting group. Deprotecting methodologies may be found in standard texts, such as T. W. Green and P. G. M. Wutz, Protective groups in organic sythesis, J. Wiley publishers, New York, N.Y., 1991, pp. 47–67.

The base salts of a compound of formula II may be formed by conventional techniques involving contacting a compound of formula II free acid with a metal base or with an amine. Suitable metal bases include hydroxides, carbonates and bicarbonates of sodium, potassium, lithium, calcium, barium, magnesium, zinc, and aluminum; and suitable amines include triethylamine, ammonia, lysine, arginine, N-methylglucamine, ethanolamine, procaine, benzathine, dibenzylamine, tromethamine (TRIS), chloroprocaine, choline, diethanolamine, triethanolamine and the like. The base salts may be further purified by chromatography followed by lyophilization or crystallization.

Compounds of the present invention are phosphonooxymethyl ether pharmaceuticals such as camptothecin, propofol, etoposide, tocopherol, etc. The pharmaceutically acceptable salt forms exhibit improved water solubility over parent compounds thereby allowing more convenient pharmaceutical formulations. Without being bound by theory, it is believed that the phosphonooxymethyl ethers of the present invention are prodrugs of the parent pharmaceuticals; the phosphonooxyethyl moiety being cleaved upon contact with. phosphatase in vivo to generate subsequently the parent compound. As shown above, compounds of the instant invention are effective pharmaceutical or therapeutic agents.

For example, compounds of formula II of the present invention may be used in a manner similar to that of camptothecin. The structure of the camptothecin prodrug is shown above. Therefore, an oncologist skilled in the art of cancer treatment will be able to ascertain, without undue experimentation, an appropriate treatment protocol for administering a compound of the present invention. The dosage, mode and schedule of administration of compounds of this invention are not particularly restricted, and will vary with the particular compound employed. Thus a compound of the formula II may be administrated via any suitable route of administration, preferable parenterally; the dosage may be, for example, in the range of about 0.1 to about 100 mg/kg of body weight, or about 5 to 500 mg/m2. Compounds of formula II may also be administrated orally; oral dosage may be in the range of about 5 to about 500 mg/kg of body weight. The actual dose used will vary according to the particular composition of formulated, the route of administration, and the particular site, host and type of tumor being treated. Many factors that modify the action of the drug will be taken into account in determining the dosage including age, sex, diet and the physical conditions of the patient.

Another example is the propofol prodrug according to formula I of the present invention. The structure of the propofol prodrug is shown below:

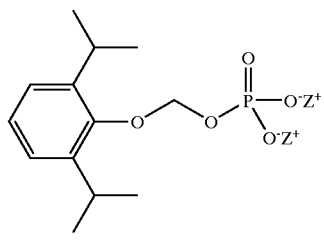

Propofol Prodrug

In the above formula for the propofol prodrug, Z is the same as defined above for formula II. Therefore, an anesthesiologist skilled in the art of anesthesia will be able to ascertain, without undue experimentation, an appropriate treatment protocol for administering a compound of the present invention. The dosage, mode and schedule of administration of compounds of this invention are not particularly restricted, and will vary with the particular compound employed. Thus, a compound of formula I such as the propofol prodrug may be administered via any suitable route of administration, preferably parenterally; the dosage may be, for example, in the range of 0.5 to 10 mg/kg administered according to procedures for induction of general anesthesia or maintenance of general anesthesia. Alternatively, the compound of formula I may be administered by parenteral infusion, the dosage may be, for example, in the range of 2 μg/kg/min to 800 μg/kg/min administered according to procedures for maintenance of general anesthesia, initiation and maintenance of MAC sedation or initiation and maintenance of ICU sedation.

The present invention also provides pharmaceutical compositions containing a pharmaceutically effective amount of compound of formula I in combination with one or more pharmaceutically acceptable carriers, excipients, diluents or adjuvants. For example, compounds of the present invention may be formulated in the form of tablets, pills, powder mixtures, capsules, injectables, solutions, suppositories, emulsions, dispersions, food premix, and in other suitable forms. They may also be manufactured in the form of sterile solid compositions, for example, freeze-dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use of parenteral administration.

Typical of pharmaceutically acceptable carriers are, for example, manitol, urea, dextrans, lactose, non-reducing sugars, potato and maize starches, magnesium stearate, talc, vegetable oils, polyalkylene glycols, ethyl cellulose, poly(vinyl-pyrrolidone), calcium carbonate, ethyloleate, isopropyl myristate, benzyl benzoate, sodium carbonate, gelatin, potassium carbonate, silicic acid. The pharmaceutical preparation may also contain non toxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

In the following experimental procedures, all temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiplet (m), doublet (d), quartet (q), triplet (t), doublet of doublets (dd), doublet of triplet (dt), and doublet of quartet (dq). The solvents employed for taking NMR spectra are acetone-d6 (deuterated acetone) DMSO-d6 (perdeuterodimethylsulfoxide), $D_2O$ (deuterated water), CDCl3 (deuterochloroform) and other conventional deuterated solvents.

The abbreviations used herein are conventional abbreviations widely employed in the art. Some of which are: MS (mass spectrometry); HRMS (high resolution mass spectrometry); Ac (acetyl); Ph (phenyl); FAB (fast atom bombardment) min (minute); h or hrs (hour(s)); NIS (N-iodosuccinimide); DMSO (dimethylsulfoxide); THF (tetrahydrofuran).

The following examples are provided to illustrate the synthesis of representative compounds of the instant invention and are not to be construed as limiting the scope of the invention in any manner. One skilled in the art will be able to adapt these methods, without undue experimentation, to the synthesis of compounds within the scope of this invention but not specifically disclosed. For example, in the following examples, specific salts are employed, however, these salts are not to be construed as limiting. An example of this situation is the repeated use of a silver salt of dibenzylphosphate. Tetralkyl ammonium salts, such as tetramethyl ammonium salts or other alkali metal salts may be used in lieu of the silver salt.

EXAMPLES

I. Synthesis of O-Phosphonooxymethylpropofol

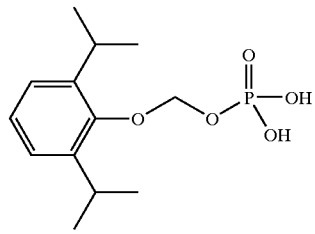

Ia. Synthesis of O-methylthiomethylpropofol

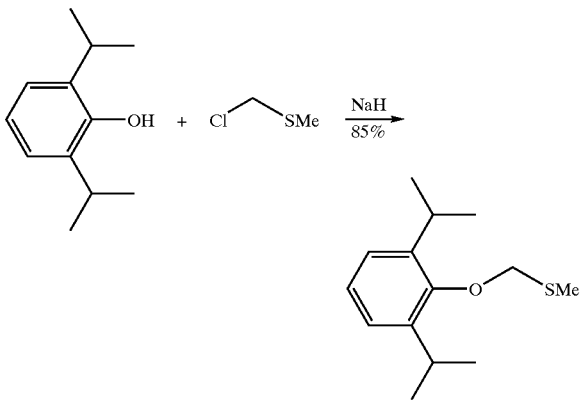

To a stirred suspension of sodium hydride (150 mg, 6.2 mmol) in dry HMPA (10 mL), kept under an argon atmosphere, was added dropwise propofol (1.1 mL of 97%, 5.7 mmol) over 15 minutes. The reaction mixture was then stirred at room temperature for an additional 30 minutes. To this mixture was added dropwise chloromethyl methyl sulfide (550 μl of 95%, 6.2 mmol) and then stirred at room temperature. After 20 hours, the reaction mixture was partitioned with stirring between water (10 mL) and benzene (20 mL). The aqueous layer was separated and extracted with benzene (10 mL). The benzene fractions were combined, washed with water (2×3 mL), dried over sodium sulfate, and evaporated under reduced pressure. The resulting oily residue was subjected to column chromatography (silica gel, hexane, then 4:1 hexane/chloroform) to give 1.15 g (85% yield) of the title compound as a colorless oil.

EIMS: [M+], m/z 238.

$^1$H NMR (300 MHz, CDCl$_3$, δ): 1.24 (d, J=6.9 Hz, 12H), 2.37 (s, 3H), 3.37 (hept, J=6.9 Hz, 2H), 4.86 (s, 2H), 7.12 (s, 3H). $^{13}$C NMR (75 MHz, CDCl$_3$, δ): 15.40, 23.98, 26.68, 78.12, 124.04, 125.05, 141.74, 152.20.

Ib. Synthesis of O-chloromethylpropofol

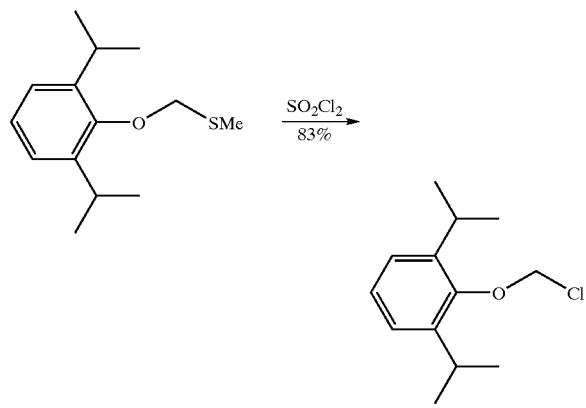

To a stirred solution of O-methylthiomethylpropofol (3.00 g, 12.5 mmol) in dry methylene chloride (30 mL), kept under an argon atmosphere, was added a 1M solution of $SO_2Cl_2$ in dry methylene chloride (12.2 mL, 12.2 mmol) at 5° C. over five minutes. The reaction mixture was stirred for 10 minutes at the same temperature and then for three hours at room temperature. The solvent was evaporated under reduced pressure and the brown residual oil was purified by flash column chromatography (silica gel, 1:20 hexane/ethyl acetate) to give 2.36 g (83% yield) of the title compound as a yellow oil.

CIMS $(NH_3)$: $[M]^+$, m/z 226, $[MH+NH_3]^+$, m/z 244.

$^1$H NMR (300 MHz, $CDCl_3$, δ): 1.22 (d, J=6.9 Hz, 12H), 3.35 (hept, J=6.9 Hz, 2H), 5.76 (s, 2H), 7.15 (m, 3H). $^{13}$C NMR (75 MHz, $CDCl_3$, δ) 23.93, 26.84, 83.34, 124.34, 125.95, 141.34, 150.93.

Ic. Synthesis of O-phosphonooxymethylpropofol dibenzyl ester (Route-1)

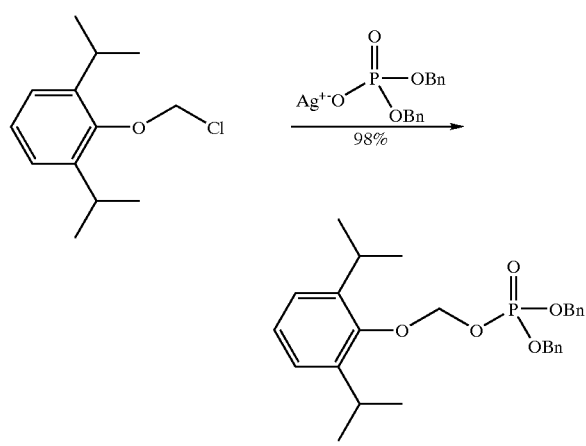

A mixture of O-chloromethylpropofol (2.20 g, 9.7 mmol), silver dibenzylphosphate (3.85 g, 10.0 mmol) and dry toluene (50 mL) was refluxed under an argon atmosphere for 45 minutes. The mixture was cooled down to room temperature and filtered. After the solvent was evaporated in vacuo, the oily residue was purified by silica gel flash column chromatography (9:1 hexane/ethyl acetate and then 1:1 hexane/ethyl acetate) to give 4.43 g (98% yield) of the title compound as a yellow oil.

CIMS $(NH_3)$: $[MH]^+$, m/z 469, $[MH+NH3]^+$, m/z 486.

$^1$H NMR (300 MHz, $CDCl_3$, δ): 1.17 (d, J=6.8 Hz, 12H), 3.33 (hept, J=6.9 Hz, 2H), 5.00 (d, J=7.8 Hz, 2H), 5.01 (d, J=7.8 Hz, 2H), 5.42 (d, J=9.9 Hz, 2H), 7.12 (m, 3H), 7.32 (m, 10H). $^{13}$C NMR (75 MHz, $CDCl_3$, δ): 23.79, 26.57, 69.15, 69.23, 94.14, 94.20, 124.07, 125.62, 127.70, 128.44, 135.42, 135.51, 141.50, 151.07.

Ic. Synthesis of O-phosphonooxymethylpropofol dibenzyl ester (Alternate Route-1)

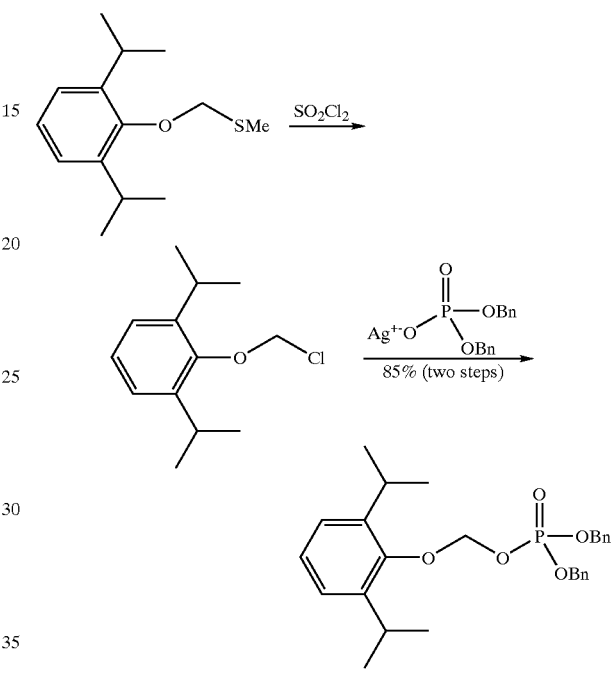

To a stirred solution of O-methylthiomethylpropofol (1.45 g, 6.08 mmol) in dry methylene chloride (15 mL) under an argon atmosphere at 0–5° C. was added a 1M solution of $SO_2Cl_2$ in dry methylene chloride (6.5 mL, 6.5 mmol) over five minutes. The reaction mixture was stirred for 10 minutes at 5° C. and three hours at room temperature. Then the solvent was evaporated under reduced pressure. The residual oil was dissolved in toluene (ACS-grade, 20 mL); silver dibenzylphosphate (3.50 g, 9.1 mmol) was added, and the resulting mixture was refluxed for 45 minutes. The brown reaction mixture was cooled down to room temperature and filtered. After the solvent was evaporated in vacuo, the oily residue was purified by silica gel flash column chromatography (9:1 hexane/ethyl acetate, then 1:1 hexane/ethyl acetate) to give 2.41 g (85% yield) of the title compound as a yellow oil. This product had the same Rf (TLC) and $^1$H NMR spectrum (300 MHz, $CDCl_3$) as an authentic sample.

Ic. Synthesis of O-phosphonooxymethylpropofol dibenzyl ester (Alternate Route-2)

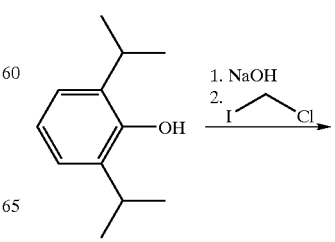

-continued

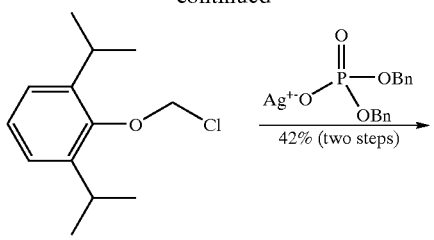

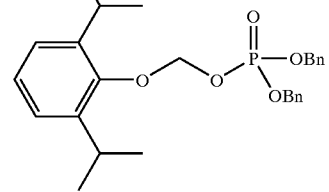

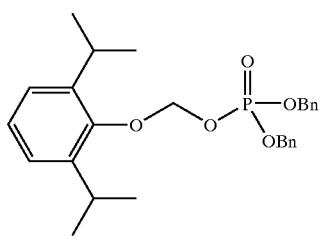

To a stirred suspension of sodium hydride (41 mg of 60% dispersion in mineral oil, 1.02 mmol) in dry dimethoxyethane (1.5 mL) under an argon atmosphere was added dropwise propofol (200 µl of 97%, 1.04 mmol) over 5 minutes and the resulting mixture was stirred for an additional 15 minutes. The resulting homogeneous solution was added dropwise to a stirred solution of chloroiodomethane (4.0 mL, 53 mmol) in dry dimethoxyethane (4 mL) over 15 minutes. This reaction mixture was stirred for two hours, filtered, and then the solvent and the excess of chloroiodomethane were evaporated. The residual oil was dissolved in toluene (HPLC-grade, 10 mL). To this solution was added silver dibenzylphosphate (400 mg, 1.04 mmol), and the resulting mixture was refluxed for 10 minutes. After the reaction mixture was cooled down to room temperature and filtered, the solvent was evaporated in vacuo. The oily residue was purified by silica gel flash column chromatography (9:1 hexane/ethyl acetate and then 1:1 hexane/ethyl acetate) to give 205 mg (42% yield) of the title compound as a yellow oil. This product had the same Rf (TLC) and $^1$H NMR spectrum (300 MHz, CDCl$_3$) as an authentic sample.

Further to the above reaction Ic (alternate route-2) it is understood that other reagents may be used depending on the desired compound. For example, when, a compound of formula I wherein n=2 is desired, the chloroiodomethane may be substituted with a compound such as X—CH2-O—CH2-Cl, wherein X is a good leaving group.

Ic. Synthesis of O-phosphonooxymethylpropofol dibenzyl ester (Alternate Route-3)

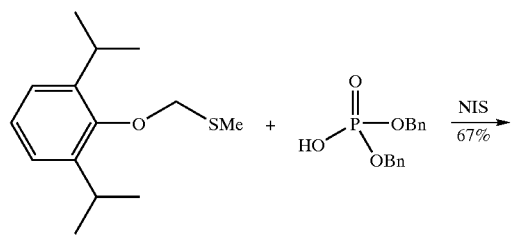

To a stirred solution of O-methylthiomethylpropofol (91 mg, 0.38 mmol) in dry methylene chloride (2 mL) under an argon atmosphere were added powdered, activated 4Å molecular sieves (100 mg), and then a solution of dibenzylphosphate (127 mg, 0.45 mmol) and N-iodosuccinimide (102 mg of 95%, 0.43 mmol) in tetrahydrofuran (2 mL). The reaction mixture was stirred at room temperature for one hour, filtered, and diluted with methylene chloride (30 mL). The resulting solution was washed with a solution of sodium thiosulfate (2 mL of a 1M solution), a saturated solution of sodium bicarbonate (3 mL), brine (5 mL), dried over a mixture of sodium sulfate and magnesium sulfate, filtered, and concentrated in vacuo. The oily residue was purified by silica gel flash column chromatography (1:1 hexane/ethyl acetate) to give 120 mg (67% yield) of the title compound as a yellow oil. This product had the same R$_f$ (TLC) and $^1$H NMR spectrum (300 MHz, CDCl$_3$) as an authentic sample.

Ic. Synthesis of O-phosphonooxymethylpropofol dibenzyl ester (Alternate Route-4)

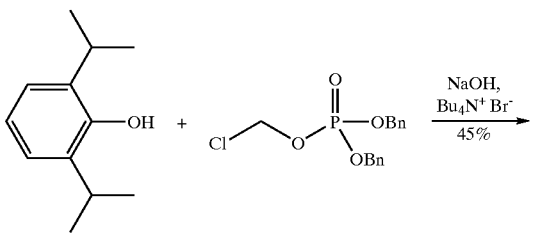

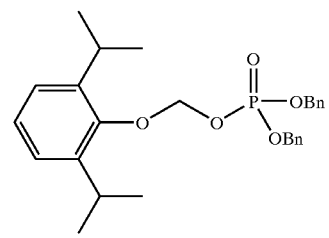

To a solution of propofol (38 mg of 97%, 0.21 mmol) in methylene chloride (1 mL) was added tetrabutylammonium bromide (10 mg, 0.03 mmol) and a solution of sodium hydroxide (40 mg, 1 mmol) in water (0.2 mL). The heterogeneous mixture was stirred for 15 minutes. Then a solution of chloromethyl dibenzylphosphate (104 mg, 0.32 mmol) in methylene chloride (1 mL) was added and the reaction mixture was stirred vigorously for eight hours. The mixture was then diluted with methylene chloride (10 mL), washed with water (2 mL), dried over sodium sulfate, filtered, and evaporated in vacuo. The oily residue was purified by silica gel flash column chromatography (hexane, 20:1 hexane/ethyl acetate, and 10:1 hexane/ethyl acetate) to give 44 mg (45% yield) of the title compound as a yellow oil. This product had the same R$_f$ (TLC) and $^1$H NMR spectrum (300 MHz, CDCl$_3$) as an authentic sample.

Further to the above reaction Ic (alternate route-4) it is to be understood that the reagent:

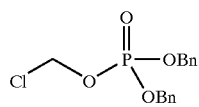

can be generically represented by the following formula:

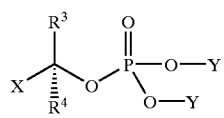

wherein X represents a leaving group, R3 and R4 are each a hydrogen atom, an organic group or an inorganic group and Y is a phosphate protecting group. Examples of leaving groups include chlorine, bromine, iodine, tosylate or any other suitable leaving group. Examples of phosphate protecting groups include protecting groups that temporarily block the reactivity of the phosphate group and permit selective displacement with the nucleophilic displacement reaction. Examples of such blocking groups include but are not limited to benzyl, allyl, tertiary butyl and isopropyl, ethyl and β-cyanoethyl.

Ic. Synthesis of O-phosphonooxymethylpropofol dibenzyl ester (Alternate Route-5)

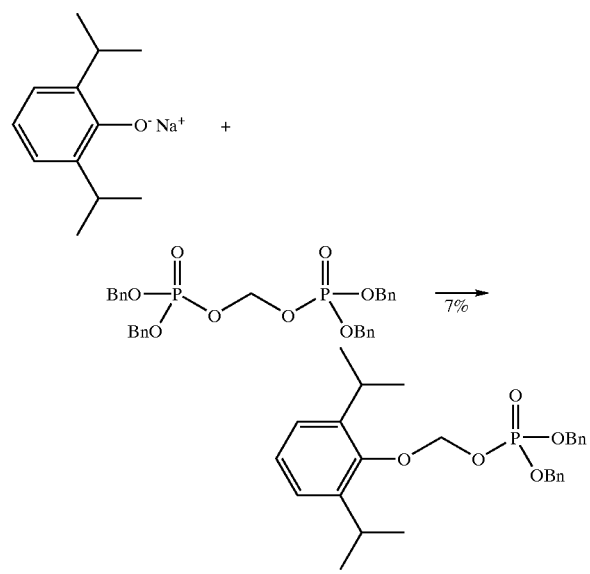

To a stirred suspension of sodium hydride (36 mg of a 60% dispersion in mineral oil, 0.91 mmol) in dry dimethoxyethane (2 mL) under an argon atmosphere was added dropwise propofol (172 μl of 97%, 0.90 mmol) over five minutes. The resulting mixture was stirred at room temperature for an additional 20 minutes. To the mixture was then added the solution of formaldehyde bis-(dibenzylphosphono)acetal (500 mg, 0.88 mmol) in dry dimethoxyethane (3 mL). The reaction mixture was stirred at room temperature for 20 hours and then at 70° C. for 2.5 hours. The mixture was then filtered and the solvent was evaporated in vacuo. The oily residue was purified by silica gel flash column chromatography (hexane, 10:1 hexane/ethyl acetate, and then 1:1 hexane/ethyl acetate) to give 29 mg (7% yield) of the title compound as a yellow oil. This product had the same $R_f$(TLC) and $^1$H NMR spectrum (300 MHz, CDCl$_3$) as an authentic sample.

Id. Synthesis of O-phosphonooxymethylpropofol

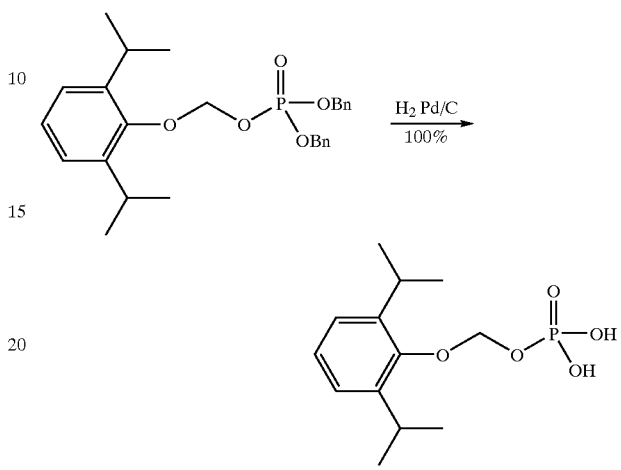

To a solution of O-phosphonooxymethylpropofol dibenzyl ester (115 mg, 0.245 mmol) in methanol (10 mL) was added palladium on carbon (10%, 20 mg). This mixture was stirred under an atmosphere of hydrogen (1 atm) for 1.5 hour. The catalyst was removed by filtration through Celite, and the filtrate was evaporated at reduced pressure to give 70.5 mg (100% yield) of the title compound as a colorless oil, unstable on standing at room temperature.

FABMS-(GLY): [M–H]$^-$, m/z 287.

$^1$H NMR (300 MHz, acetone-d$_6$, δ): 1.19 (d, J=6.8 Hz, 12H), 3.46 (sext, J=6.8 Hz, 2H), 5.45 (d, J=9.7 Hz, 2H), 7.15 (m, 3H). $^{13}$C NMR (75 MHz, acetone-d$_6$, δ): 24.2178, 27.1496, 94.63, 94.65, 124.08, 126.30, 142.46, 152.32.

Ie. Synthesis of O-phosphonooxymethylpropofol disodium salt

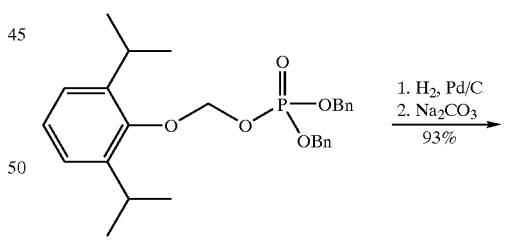

To a solution of O-phosphonooxymethylpropofol dibenzyl ester (1.05 g, 2.24 mmol) in tetrahydrofuran (100 mL) was added water (5 mL) and palladium on carbon (10%, 300 mg). This mixture was stirred under hydrogen (1 atm) for one hour. The catalyst was removed by filtration through Celite, and the filtrate was treated with a solution of sodium carbonate hydrate (263 mg in 3 mL of water, 2.12 mmol). THF was evaporated under reduced pressure and the residual water solution was extracted with ether (3×3 mL). The aqueous layer was evaporated to dryness (argon stream or rotary evaporator) and the resulting solid was dried overnight in vacuo, washed with ether (4×4 mL), hexane (2×4 mL), and again dried in vacuo to provide 655 mg (93% yield) of the title compound as a white powder.

FABMS-(GLY): [M−2Na̅+H]—, m/z 287.

$^1$H NMR (300 MHz, D$_2$O, δ): 1.22 (d, J=7.0 Hz, 12H), 3.46 (hept, J=6.9 Hz, 2H), 5.27 (d, J=7.5 Hz, 2H), 7.28 (m, 3H).

II. Synthesis of O-Phosphonooxymethyl-alpha-tocopherol

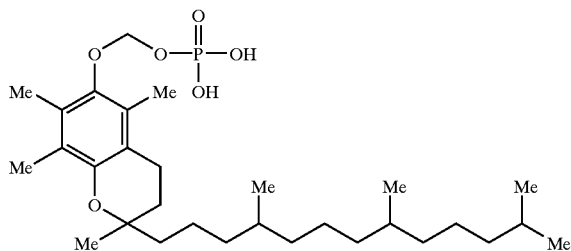

IIa. Synthesis of O-phosphonooxymethyl-alpha-tocopherol dibenzyl ester

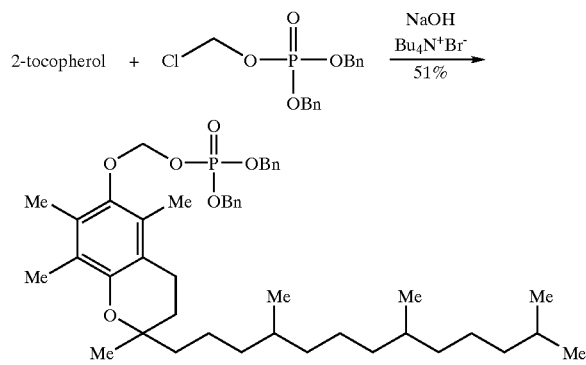

To a solution of chloromethyl dibenzylphosphate (323 mg, 0.98 mmol), alphatocopherol (409 mg of 97%, 0.92 mmol), and tetrabutylammonium bromide (301 mg, 0.92 mmol) in benzene (5 mL) was added an aqueous solution of sodium hydroxide (150 mg in 0.2 mL of water, 3.7 mmol). The resulting reaction mixture was vigorously stirred at room temperature for two hours under an argon atmosphere. The mixture was then diluted with benzene (10 mL), washed with water (3×3 mL), dried over magnesium sulfate, filtered, and evaporated under reduced pressure. The brown oily residue was purified by silica gel flash column chromatography (10:1 hexane/ethyl acetate) to give 336 mg (51% yield) of the title compound as a yellow oil.

FABMS+(NBA): [M]$^+$, m/z 720.

$^1$H NMR (500 MHz, CDCl$_3$, δ): 0.85 (m, 12H), 1.21 (s, 3H), 1.27 (m, 24H), 1.75 (m, 2H), 2.06 (s, 3H), 2.11 (s, 3H), 2.14 (s, 3H), 2.54 (t, J=6.8 Hz, 2H), 4.97 (m, 4H), 5.20 (d, J=9.3 Hz, 2H), 7.31 (m, 10H).

IIb. Synthesis of O-phosphonooxymethyl-alpha-tocopherol

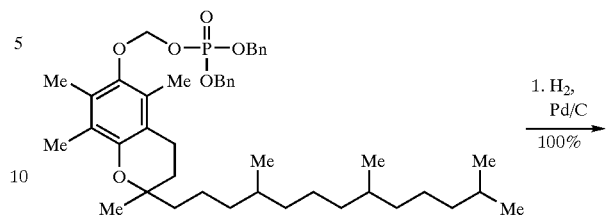

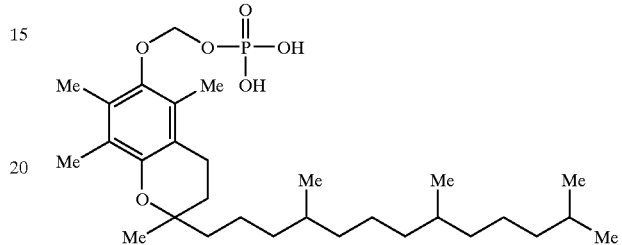

To a solution of O-phosphonooxymethyl-alpha-tocopherol dibenzyl ester (88 mg, 0.12 mmol) in tetrahydrofuran (10 mL) was added palladium on carbon (10%, 15 mg). The mixture was stirred under an atmosphere of hydrogen (1 atm) for 10 minutes (the reaction was complete after 5 minutes as judged by TLC). The catalyst was removed by filtration through Celite, the filtrate was evaporated at reduced pressure, and then dried in vacuo. The title compound was obtained in an amount of 70 mg (100% yield) as a brownish oil, which was unstable at room temperature.

FABMS+(NBA): [M]$^+$, m/z 540, [M +Na]$^+$, m/z 563; (NBA+Li) [M +Li]$^+$, m/z 547

IIc. Synthesis of O-phosphonooxymethyl-alpha-tocopherol disodium salt

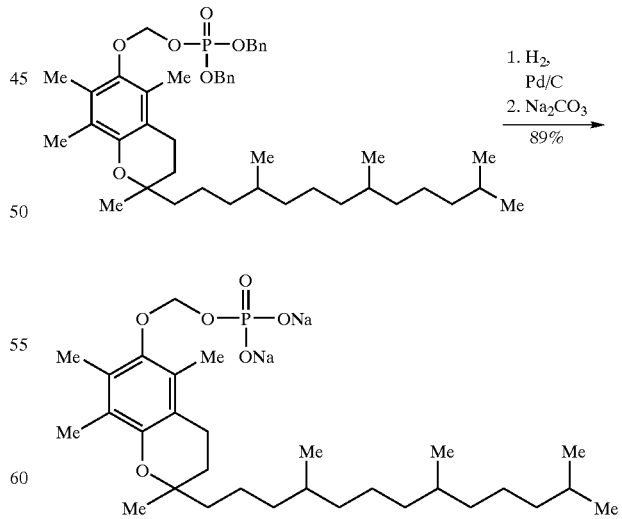

To a solution of O-phosphonooxymethyl-alpha-tocopherol dibenzyl ester (100 mg, 0.14 mmol) in tetrahydrofuran (10 mL) was added palladium on carbon (10%, 18 mg). The mixture was stirred under an atmosphere of hydrogen (1 atm) for 5 minutes. The catalyst was removed by filtration through Celite, the filtrate was evaporated at room temperature at reduced pressure, and the resulting residue was dissolved in ether (2 mL). The ether solution was then treated with an aqueous solution of sodium hydroxide (11.2 mg in 100 mL of water, 0.28 mmol), and the resulting mixture was stirred at room temperature for 10 min. The ether phase was removed and the aqueous phase was washed with ether (3×3 mL) and then dried in vacuo for 20 hours to give 73 mg (89% yield) of the title compound as a gray solid.

FABMS+(TG/G): [MH]$^+$, m/z 585, [M+Na]$^+$, m/z 607

The synthesis of water soluble derivatives of camptothecin will also be further detailed as follows:

III. Synthesis of 20-O-Phosphonooxymethylcamptothecin

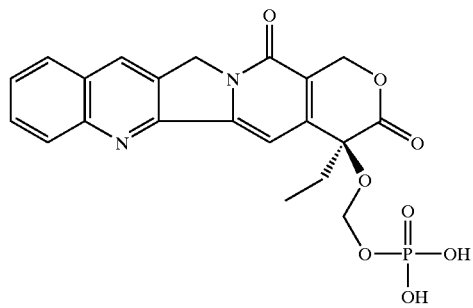

IIIa. Synthesis of 20-O-methylthiomethylcamptothecin

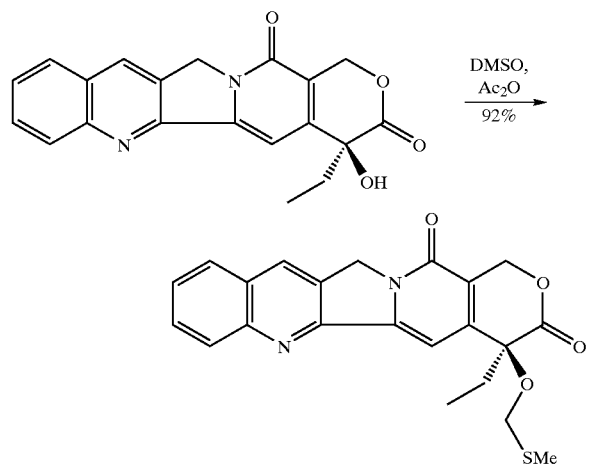

To a suspension of camptothecin (5.0 g, 14.3 mmol) in dimethylsulfoxide (250 mL) was added acetic anhydride (125 mL) and acetic acid (35 mL). The heterogeneous mixture was vigorously stirred at room temperature for 24 hours, poured into ice (800 mL), stirred for 30 minutes, and then extracted with methylene chloride (4×100 mL). The combined methylene chloride extracts were washed with water (2×100 mL) and dried over magnesium sulfate. The methylene chloride was removed at reduced pressure to give a brownish solid. The solid was dissolved in a minimum volume of methylene chloride. This solution was filtered and diluted with a 10-fold excess of hexane and then kept overnight in the refrigerator. The precipitated solid was filtered off, washed several times with hexane, and dried to give 5.38 g (92% yield) of the title compound as a light brown powder. $\alpha^D{}_{20}$–123.6° (c 0.55, CHCl$_3$).

FABMS+(NBA): [MH]$^+$, m/z 409.

$^1$H NMR (400 MHz, CDCl$_3$, δ): 0.93 (t, J=7.2 Hz, 3H), 2.11 (sext, J=7.6 Hz, 1H), 2.29 (sext, J=7.6 Hz, 1H), 2.30 (s, 3H), 4.58 (s, 2H), 5.33 (s, 2H), 5.40 (d, J=17.2 Hz, 1H), 5.62 (d, J=17.3 Hz, 1H), 7.48 (s, 1H), 7.69 (t, J=7.1 Hz, 1H), 7.86 (t, J=7.1 Hz, 1H), 7.96 (d, J=8.1 Hz, 1H), 8.25 (d, J=8.5 Hz, 1H), 8.42 (s, 1H).

$^{13}$C NMR (75 MHz, CDCl$_3$, δ): 7.76, 14.89, 33.90, 49.92, 66.68, 71.02, 76.57, 97.51, 122.63, 128.02, 128.09, 128.30, 129.71, 130.64, 131.11, 145.14, 146.10, 148.88, 152.27, 157.43, 169.34, 169.73.

IIIb. Synthesis of 20-O-phosphonooxymethylcamptothecin dibenzyl ester

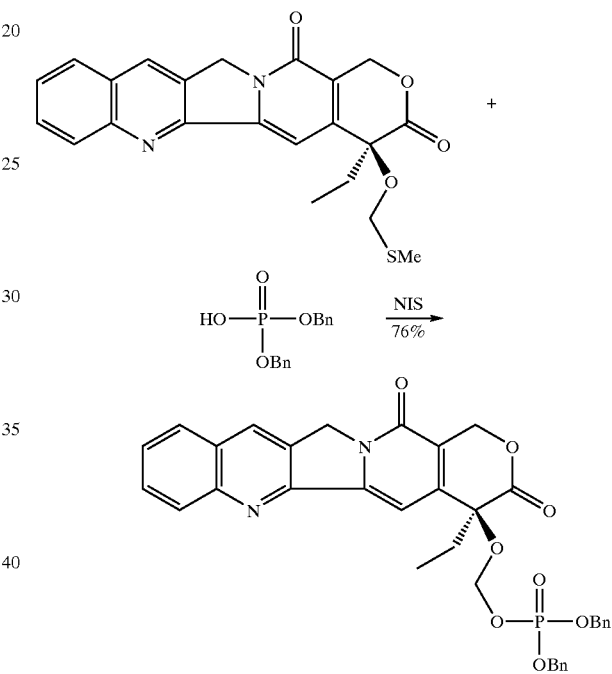

To a well stirred suspension of 20-O-methylthiomethylcamptothecin (1.00 g, 2.44 mmol) and powdered, activated 4 Å molecular sieves (5 g) in tetrahydrofuran (20 mL) was added a suspension of N-iodosuccinimide (2.00 g of 95%, 8.44 mmol) and dibenzylphosphate (2.20 g, 7.83 mmol) in methylene chloride (12 mL). The resulting mixture was vigorously stirred at room temperature for 30 minutes, filtered, and diluted with ethyl acetate (300 mL). The solution was washed with aqueous sodium thiosulfate (10%, 2×15 mL), water (2×20 mL), brine (50 mL), and dried over magnesium sulfate. The mixture was filtered and the solvent was evaporated under reduced pressure. The brown oily residue was purified by silica gel flash column chromatography (98:2 ethyl acetate/methanol) and dried in vacuo overnight to give 1.19 g (76% yield) of the title compound as a yellow foam. $\alpha^D{}_{20}$–43.1° (c 0.55, CHCl$_3$).

FABMS+(NBA): [MH]$^+$, m/z 639.

$^1$H NMR (400 MHz, CDCl$_3$, δ): 0.91 (t, J=7.4 Hz, 3H), 2.09 (sext, J=7.4 Hz, 1H), 2.26 (sext, J=7.4 Hz, 1H), 5.06 (m, 4H), 5.28 (m, 3H), 5.35 (d, J=17.0 Hz, 1H), 5.48 (2xd, J=10.5 Hz, 1H), 5.64 (d, J=17.3 Hz, 1H), 7.59 (s, 1H), 7.67 (t, J=7.0 Hz, 1H), 7.80 (t, J=7.1 Hz, 1H), 7.94 (d, J=8.0 Hz, 1H), 8.13 (d, =8.5 Hz, 1H), 8.35 (s, 1H).

$^{13}$C NMR (100 MHz, CDCl$_3$, δ): 7.73, 29.53, 32.49, 49.86, 66.74, 69.37, 69.44, 78.48, 88.99, 89.04, 98.09, 121.55, 127.65, 127.70, 127.90, 128.01, 128.25, 128.35, 128.36, 129.62, 130.48, 130.97, 135.45, 135.55, 145.47, 145.82, 148.76, 152.15, 157.18, 168.67.

IIIc. Synthesis of 20-O-phosphonooxymethylcamptothecin

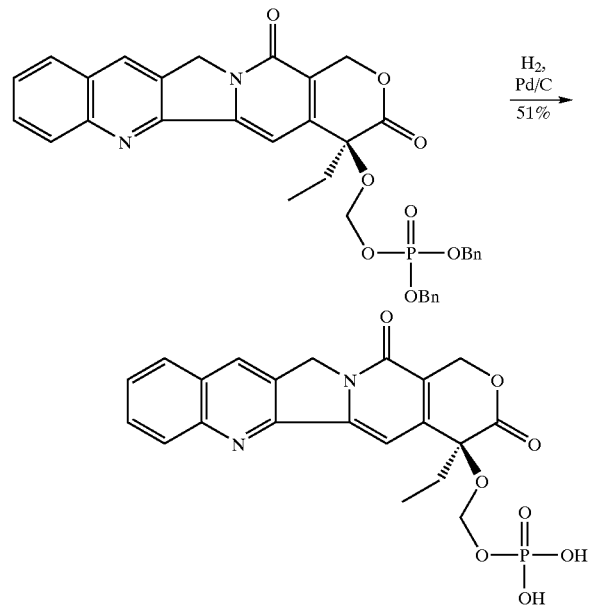

To a solution of 20-O-phosphonooxymethylcamptothecin dibenzyl ester (500 mg, 0.78 mmol) in tetrahydrofuran (100 mL) and water (5 mL) was added palladium on carbon (10%, 500 mg). This mixture was stirred under an atmosphere of hydrogen (1 atm) for 35 minutes. The catalyst was removed by filtration through Celite. The Celite was then washed with tetrahydrofuran (300 mL) and the combined filtrates were evaporated at reduced pressure. The resulting green solid was washed with ether (2×20 mL), hexane (50 mL), dried in vacuo, and then dissolved in hot methanol (60 mL). The solution was filtered, concentrated at reduced pressure to ~10 mL volume. After standing at room temperature for one hour, the solution was placed in the refrigerator overnight. The crystalline precipitate that had formed overnight was filtered off and dried in vacuo to give 155 mg of the title compound as a yellow solid. The filtrate was concentrated to ~1 mL volume and kept in the refrigerator for one hour to give an additional 28 mg of the product. Total yield: 183 mg (51%).

FABMS+(NBA): [MH]$^+$, m/z 459, [M +Na]$^+$, m/z 481.

$^1$H NMR (400 MHz, D$_2$O, δ): 0.95 (t, J=7.5 Hz, 3H), 2.25 (m, 2H), 4.98 (d, J=5.0 Hz, 2H), 5.14 (2xd, J=9.3 Hz, 1H), 5.22 (2xd, J=8.9 Hz, 1H), 5.48 (d, J=17.0 Hz, 1H), 5.60 (d, J=16.9 Hz, 1H), 7.54 (s, 1H), 7.56 (t, J=7.7 Hz, 1H), 7.77 (t, J=7.2 Hz, 1H), 7.86 (d, J=8.2 Hz, 1H), 8.01 (d, J=8.5 Hz, 1H), 8.44 (s, 1H).

Chemical structure and purity of the product were also confirmed by $^1$H NMR spectroscopy of its disodium salt, formed from the acid and two mole equivalents of sodium bicarbonate in D$_2$O.

IIIc. Synthesis of 20-O-phosphonooxymethylcamptothecin (Alternate Run)

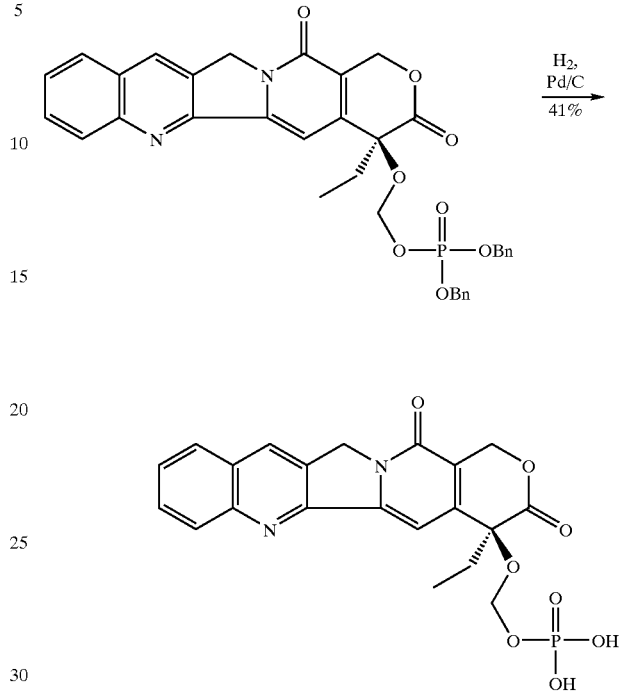

To a solution of 20-O-phosphonooxymethylcamptothecin dibenzyl ester (500 mg, 0.78 mmol) in tetrahydrofuran (100 mL) and water (5 mL) was added palladium on carbon (10%, 500 mg). The mixture was stirred under an atmosphere of hydrogen (1 atm) for 30 minutes. The catalyst was removed by filtration through Celite. Celite was washed with tetrahydrofuran (2×100 mL), and the combined filtrates were treated with an aqueous solution of sodium carbonate hydrate (97 mg in 2 mL water, 0.78 mmol). THF was evaporated at reduced pressure and the heterogeneous aqueous residue was diluted with water (10 mL) and extracted with ethyl acetate (2×3 mL). The resulting yellow homogeneous solution was acidified with hydrochloric acid (10%) to pH=1. The resulting precipitate was filtered off and dried in vacuo overnight to give 145 mg (41% yield) of the title compound as a yellow solid.

IIId. Synthesis of 20-O-phosphonooxymethylcamptothecin disodium salt

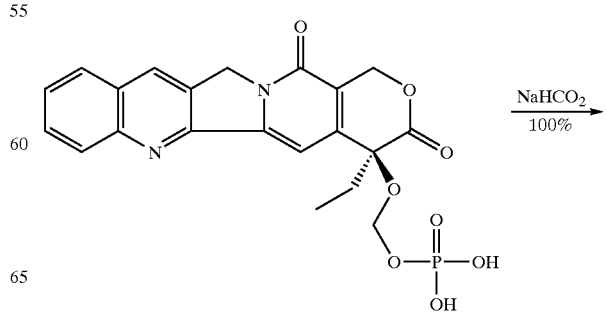

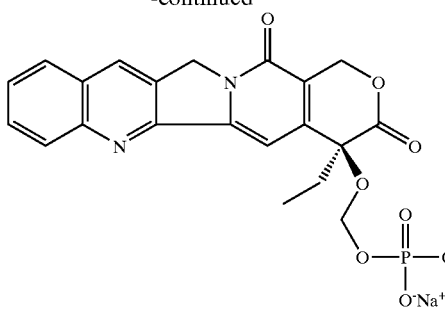

To a suspension of 20-O-phosphonooxymethylcamptothecin (5 mg, 10.9 μmol) in deuterium oxide (0.5 mL) was added a deuterium oxide solution of sodium bicarbonate (50 μl of 0.44 M solution=22 μmol). The heterogeneous mixture was sonicated for a few minutes to give a yellow homogenous solution of the title product. $^1$H NMR (400 MHz, D$_2$O, after 10 min., 96% lactone, 4% carboxylate, δ): 1.05 (t, J=7.2 Hz, 3H), 2.27 (m, 2H), 4.57 (d, J=18.8 Hz, 1H), 4.70 (d, J=18.9 Hz, 1H), 5.06 (dd, J=8.3, J=5.4 Hz, 1H), 5.18 (dd, J=7.6, J=5.5 Hz, 1H), 5.45 (d, J=16.7 Hz, 1H), 5.59 (d, J=16.8 Hz, 1H), 7.34 (t, J=7.1 Hz, 1H), 7.41 (s, 1H), 7.60 (m, 2H), 7.81 (d, J=8.3 Hz, 1H), 8.17 (s, 1H).

IIId. Synthesis of 20-O-phosphonooxymethylcamptothecin disodium salt (Alternate Run 1)

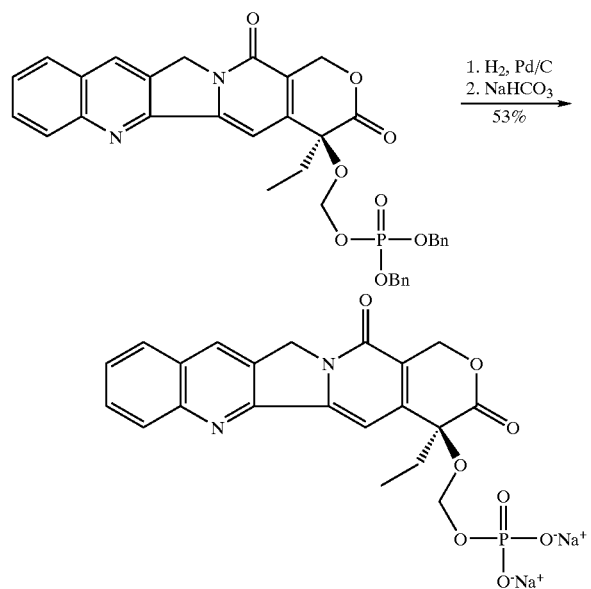

To a solution of 20-O-phosphonooxymethylcamptothecin dibenzyl ester (78 mg, 0.122 mmol) in tetrahydrofuran (10 mL) and water (3 mL) was, added palladium on carbon (10%, 80 mg). The mixture was stirred under an atmosphere of hydrogen (1 atm) for 30 minutes. The catalyst was removed by filtration through Celite and the filtrate was treated with an aqueous solution of sodium bicarbonate (20 mg in 0.5 mL of water, 0.238 mmol). The yellow precipitate was filtered off, washed with methylene chloride, and dried in vacuo to give 35 mg (57% yield) of the title compound (light brown solid) as a mixture of its lactone form (82%) and its carboxylate form (18%) (by $^1$H NMR).

IIId. Synthesis of 20-O-phosphonooxymethylcamptothecin disodium salt (Alternate Run 2)

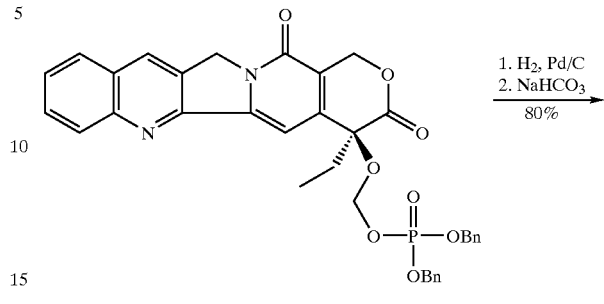

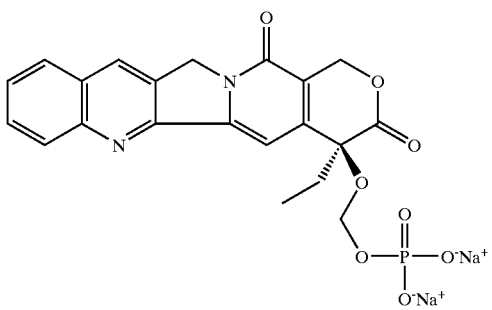

To a solution of 20-O-phosphonooxymethylcamptothecin dibenzyl ester (500 mg, 0.78 mmol) in tetrahydrofuran (100 mL) and water (5 mL) was added palladium on carbon (10%, 500 mg). This mixture was stirred under an atmosphere of hydrogen (1 atm) for 30 minutes. The catalyst was removed by filtration through Celite. Celite was washed with tetrahydrofuran (50 mL), and the combined filtrates were treated with an aqueous solution of sodium carbonate hydrate (90 mg in 2 mL of water, 0.72 mmol). Tetrahydrofuran was evaporated at reduced pressure, and the residue was dissolved in water (15 mL). The heterogeneous mixture was extracted with ethyl acetate (2×15 mL) and ether (20 mL) and the resulting aqueous homogenous solution was evaporated to dryness under a stream of argon at room temperature. The residue was dried in vacuo overnight to give 290 mg (80% yield) of the title compound (orange solid) as a mixture of its lactone form (60%), its carboxylate form (40%), and a small amount of byproducts (by $^1$H NMR).

IIIe. Synthesis of 20-O-phosphonooxymethylcamptothecin monosodium salt

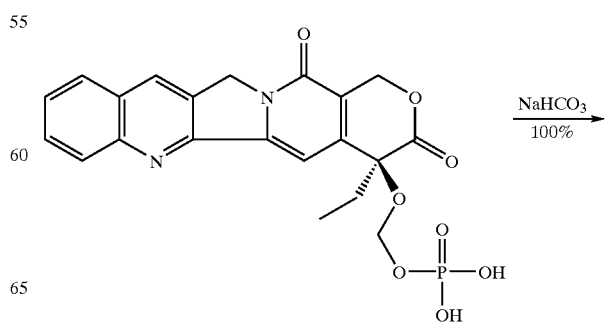

-continued

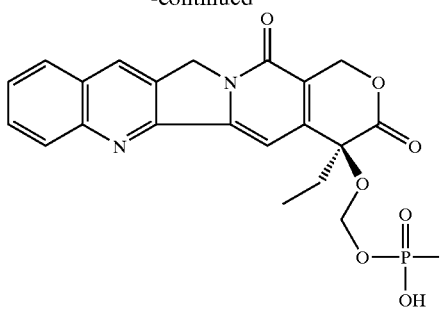

To a continuously sonicated suspension of 20-O-phosphonooxymethylcamptothecin (5 mg, 10 μmol) in deuterium oxide (0.5 mL) was added dropwise a deuterium oxide solution of sodium bicarbonate until complete homogenization was achieved (21 μl of 0.44 M solution=9.2 μmol). A yellow homogenous solution of the title compound was obtained.

$^1$H NMR (400 MHz, D$_2$O, δ): 1.00 (t, J=7.2 Hz, 3H), 2.23 (m, 2H), 4.40 (d, J=18.8 Hz, 1H), 4.50 (d, J=18.8 Hz, 1H), 5.10 (dd, J=9.7, J=5.9 Hz, 1H), 5.26 (dd, J=9.0, J=6.1 Hz, 1H), 5.39 (d, J=16.7 Hz, 1H), 5.50 (d, J=16.7 Hz, 1H), 7.20 (t, J=7.3 Hz, 1H), 7.28 (s, 1H), 7.46 (m, 2H), 7.66 (d, J=8.4 Hz, 1H), 8.02 (s, 1H).

IIIf. Synthesis of 20-O-phosphonooxymethylcamptothecin lysine salt

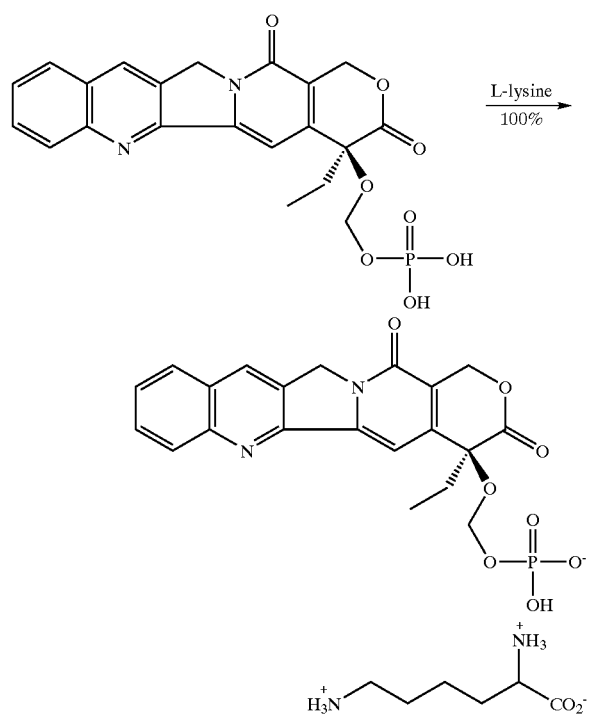

To a continuously sonicated suspension of 20-O-phosphonooxymethylcamptothecin (5 mg, 10 μmol) in deuterium oxide (0.5 mL) was added dropwise a deuterium oxide solution of L-lysine (25 μl of 0.43 M solution=10.7 μmol) until complete homogenization was achieved. A yellow homogenous solution of the title compound was obtained.

$^1$H NMR (400 MHz, D$_2$O, 94% lactone, 6% carboxylate, δ): 1.02 (t, J=7.2 Hz, 1H), 1.49 (m, 2H), 1.73 (m, 2H), 1.88 (m, 2H), 2.25 (m, 2H), 3.03 (t, J=7.5 Hz, 2H), 3.76 (t, J=6.0 Hz, 1H), 4.43 (d, J=19.0 Hz, 1H), 4.52 (d, J=18.9 Hz, 1H), 5.11 (dd, J=9.7, J=5.8 Hz, 1H), 5.27 (dd, J=9.2, J=5.8 Hz, 1H), 5.41 (d, J=16.7 Hz, 1H), 5.53 (d, J=16.7 Hz, 1H), 7.23 (t, J=7.4 Hz, 1H), 7.30 (s, 1H), 7.49 (m, 2H), 7.68 (d, J=8.4 Hz, 1H), 7.04 (s, 1H)

IIIg. Synthesis of 20-O-phosphonooxymethylcamptothecin arginine salt

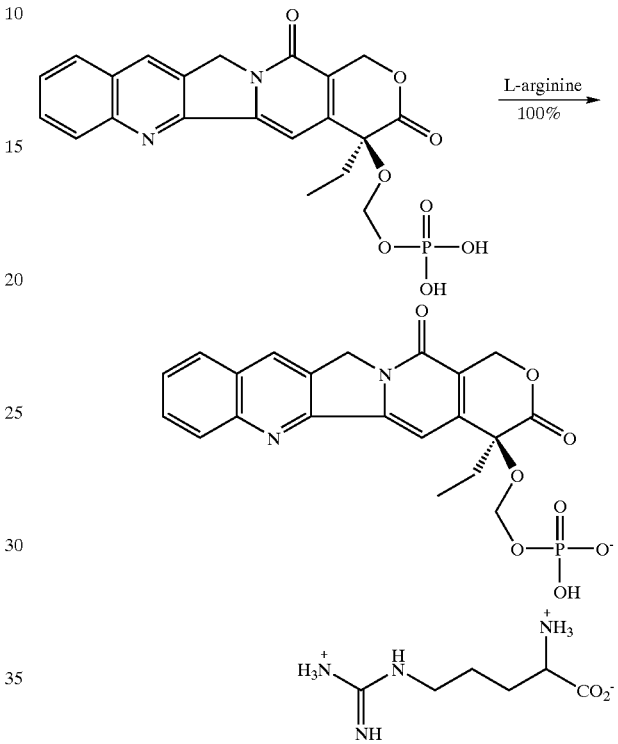

To a continuously sonicated suspension of 20-O-phosphonooxymethylcamptothecin (5 mg, 10 μmol) in deuterium oxide (0.5 mL) was added dropwise a deuterium oxide solution of L-arginine (27 μl of 0.40 M, 10.8 μmol) until complete homogenization was achieved. A yellow homogenous solution of the title compound was obtained.

$^1$H NMR (400 MHz, D$_2$O, δ): 1.02 (t, J=7.1 Hz, 1H), 1.66 (m. 2), 1.89 (m, 2H), 2.25 (m, 2H), 3.20 (t, J=6.8 Hz, 2H), 3.77 (t, J=6.0 Hz, 1H), 4.40 (d, J=19.0 Hz, 1H), 4.49 (d, J=18.8 Hz, 1H), 5.12 (dd, J=9.7, J=6.0 Hz, 1H), 5.29 (dd, J=8.8, J=6.1 Hz, 1H), 5.40 (d, J=16.7 Hz, 1H), 5.51 (d, J=16, 7 Hz, 1H), 7.20 (t, J=7.3 Hz, 1H), 7.29 (s, 1H), 7.47 (m, 2H), 7.66 (d, J=8.3 Hz, 1H), 8.03 (s, 1H).

IIIh. Synthesis of 20-O-phosphonooxymethylcamptothecin N-methylglucamine salt

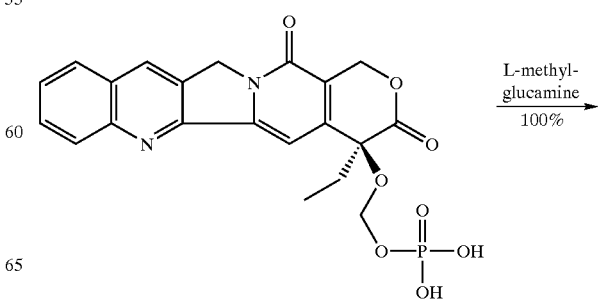

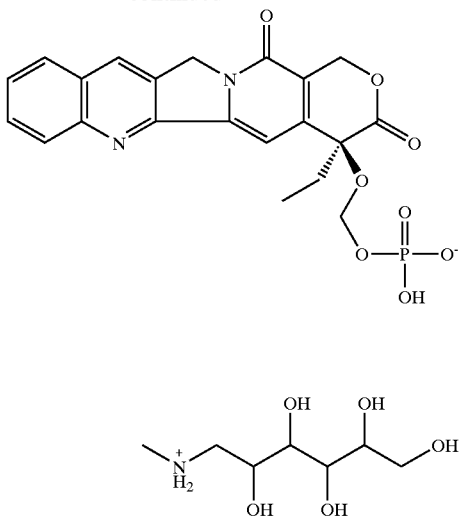

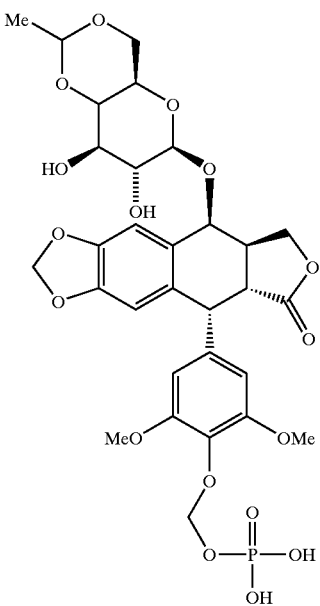

To a continuously sonicated suspension of 20-O-phosphonooxymethylcamptothecin (5 mg, 10.9 μmol) in deuterium oxide (0.5 mL) was added dropwise a deuterium oxide solution of (D)-N-methylglucamine (21 μl of 0.51 M solution=10.7 μmol) until complete homogenization was achieved. A yellow homogenous solution of the title compound was obtained.

$^1$H NMR (400 MHz, D$_2$O, δ): 1.02 (t, J=7.3 Hz, 3H), 2.25 (m, 2H), 2.78 (s, 3H), 3.20 (m, 2H), 3.65 (m, 2H), 3.80 (m, 3H), 4.11 (m, 1H), 4.44 (d, J=18.9 Hz, 1H), 4.53 (d, J=19.0 Hz, 1H), 5.12 (dd, J=9.8, J=5.9 Hz, 1H), 5.27 (dd, J=9.2, J=5.9 Hz, 1H), 5.41 (d, J=16.7 Hz, 1H), 5.53 (d, J=16.7 Hz, 1H), 7.23 (t, J=7.4 Hz, 1H), 7.49 (m, 2H), 7.69 (d, J=8.4 Hz, 1H), 8.05 (s, 1H).

IV. Synthesis of 4'-O-phosphonooxymethyletoppside

IVa. Synthesis of 4'-O-phosphonooxymethyletoposide dibenzyl ester

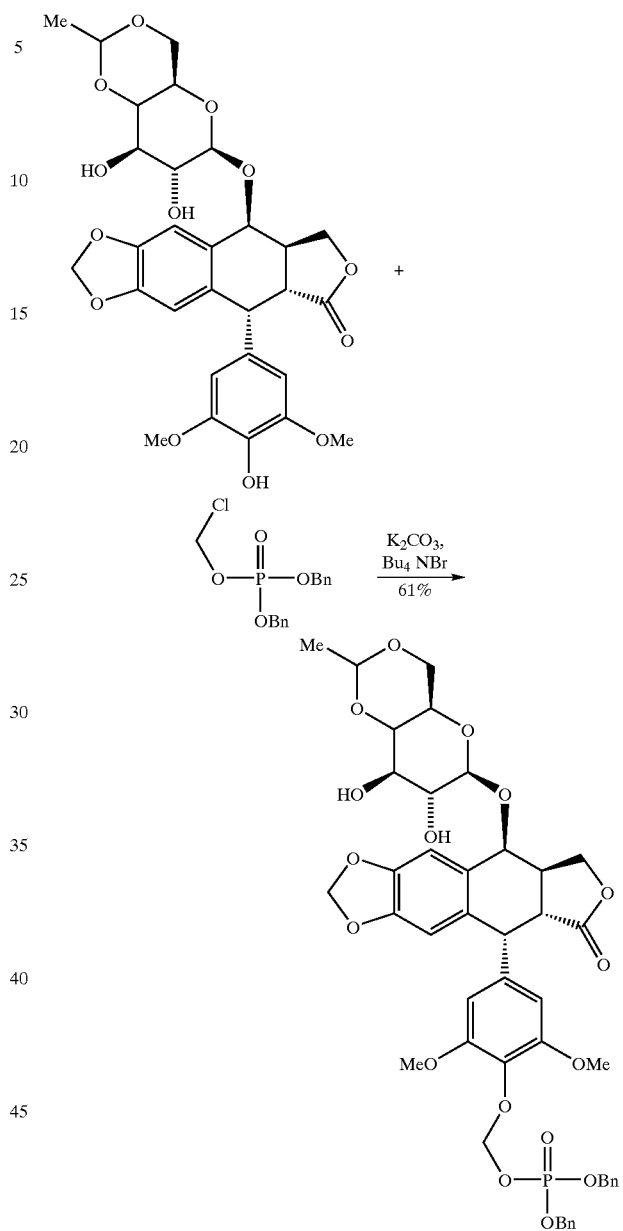

To a solution of chloromethyl dibenzylphosphate (670 mg, 2.05 mmol), etoposide (300 mg, 0.51 mmol), and tetrabutylammonium bromide (164.4 mg, 0.51 mmol) in tetrahydrofuran (0.5 mL) was added powdered potassium carbonate (352.4 mg, 2.55 mmol). The resulting reaction mixture was vigorously stirred at room temperature for 35 minutes. The mixture was then directly purified by silica gel flash column chromatography (30:1 methylene chloride/methanol) to give 272 mg (61% yield) of the title compound as a white solid with more than 95% of the trans stereochemistry retained.

FABMS+(NBA): [MH]$^+$, m/z 879.

$^1$H NMR (400 MHz, CDCl$_3$, δ): 1.41 (d, J=5.0 Hz, 3H), 2.79 (br s, 1H), 2.86 (m, 1H), 2.97 (br s, 1H), 3.30 (dd, J=14.2, J=5.3 Hz, 1H), 3.35 (m, 2H), 3.45 (t, J=8.5, J=8.0 Hz, 1H), 3.59 (m, 1H), 3.66 (s, 6H), 3.74 (m, 1H), 4.19 (m,

1H), 4.20 (t, J=8.5, J=8.0 Hz, 1H), 4.42 (dd, J=10.3, J=9.1 Hz, 1H), 4.60 (d, J=5.2 Hz, 1H),4.64(d, J=7.6Hz, 1H), 4.76 (q, J=5.0 Hz, 1H), 4.92 (d, J=3.4 Hz, 1H), 5.03 (dd, J=7.3, J=4.3 Hz, 4H), 5.54 (dd, J=11.7, J=5.1 Hz, 1H), 5.59 (dd, J=11.3, J=5.1 Hz, 1H), 5.99 (d, J =3.5 Hz, 2H), 6.26 (s, 2H), 6.51 (s, 1H), 6.84 (s, 1H), 7.33 (m, 10H).

$^{13}$C NMR (75 MHz, CDCl$_3$, δ): 20.21, 37.49, 41.00, 43.78, 56.07, 66.32, 67.87, 67.97, 69.06, 69.14, 73.01, 73.29, 74.47, 79.70, 92.55, 92.62, 99.70, 101.57, 101.72, 107.89, 109.13, 110.55, 127.82, 127.97, 128.15, 128.35, 128.43, 132.40, 133.08, 135.68, 135.78, 136.49, 147.14, 148.73, 152.18, 174.90.

IVb. Synthesis of 4'-O-phosphonooxymethyletoposide

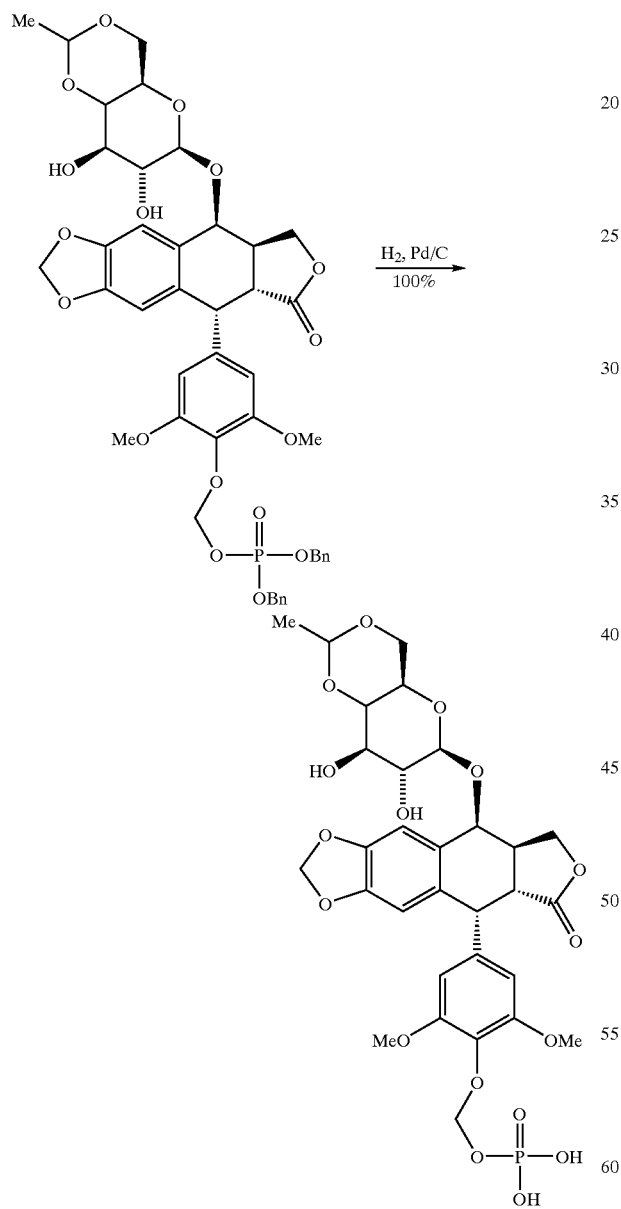

atm) for 10 minutes. The catalyst was removed by filtration through Celite, and tetrahydrofuran was evaporated at reduced pressure. The resulting residue was dried in vacuo to give 16 mg (100% yield) of the title compound as a white solid.

FABMS+(NBA): [MH]$^+$, m/z 699.

$^1$H NMR (400 MHz, CDCl$_3$/DMSO-d$_6$, δ): 1.29 (d, J=5.0 Hz, 3H), 2.78 (m, 1H), 3.21 (m, 2H), 3.29 (t, J=8.6, J=7.8 Hz, 1H), 3.37 (dd, J=14.0, J=5.3 Hz, 1H), 3.52 (m, 2H), 3.62 (s, 6H), 4.09 (m, 1H), 4.17 (t, J=8.1 Hz, 1H), 4.38 (dd, J=8.8, J=8.7 Hz, 1H), 4.44 (d, J=7.6 Hz, 1H), 4.48 (d, J=5.3 Hz, 1H), 4.66 (q, J=5.0 Hz, 1H), 4.88 (d, J=3.3 Hz, 1H), 5.05 (br s, 7H), 5.40 (dd, J=10.7, J=7.8 Hz, 1H), 5.43 (dd, J=10.4, J=7.5 Hz, 1H), 5.89 (dd, J=8.8 Hz, 1H), 6.18 (s, 2H), 6.41 (s, 1H), 6.78 (s, 1H).

IVc. Synthesis of 4'-O-phosphonooxymethyletoposide disodium salt

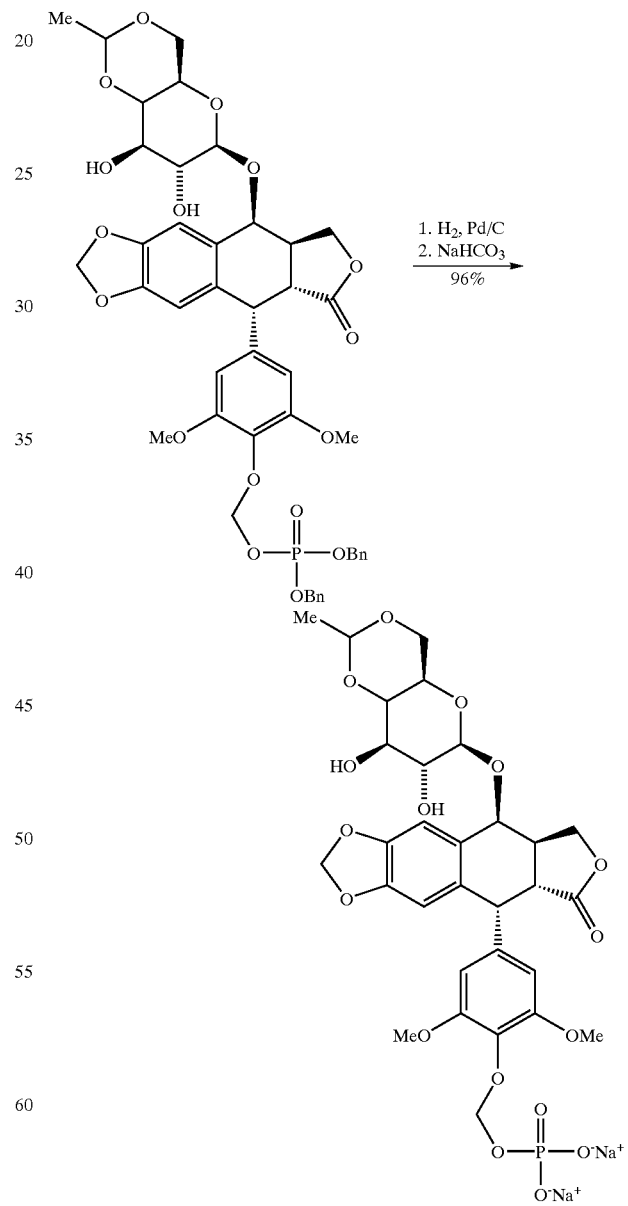

To a solution of 4'-O-phosphonooxymethyletoposide dibenzyl ester (20.5 mg, 0.023 mmol) in tetrahydrofuran (2 mL) was added palladium on carbon (10%, 5 mg). The mixture was stirred under an atmosphere of hydrogen (1

To a solution of 4'-O-phosphonooxymethyletoposide dibenzyl ester (200 mg, 0.227 mmol) in tetrahydrofuran (10 mL) was added palladium on carbon (10%, 45 mg). This mixture was stirred under an atmosphere of hydrogen (1 atm) for 25 minutes. The catalyst was removed by filtration through Celite. The filtrate was evaporated at reduced pressure, and the residue was dried in vacuo. The resulting white solid was dissolved in an aqueous solution of sodium bicarbonate (2.9 mL of 0.136 M=0.394 mmol). The resulting heterogeneous mixture was mixed with activated carbon, stirred for a few minutes, and was then filtered through a 40 µm filter unit. The homogenous, colorless filtrate was lyophilized to give 140 mg (96% yield) of the title compound as a white solid with more than 95% of bans stereochemistry retained.

FABMS+(NBA): [MH]$^+$, m/z 743, [M−Na+2H]$^+$, m/z 721, [M−2Na+3H]$^+$, m/z 699.

$^1$H NMR (400 MHz, D$_2$O, δ): 1.37 (d, J=5.1 Hz, 3H), 3.10 (m, 1H), 3.37 (dd, J=8.9, J=8.0 Hz, 1H), 3.48 (m, 2H), 3.65 (m, 3H), 3.75 (s, 6H), 4.29 (dd, J=10.4, J=4.5 Hz, 1H), 4.41 (t, J=8.3, J=8.0 Hz, 1H), 4.49 (dd, J=10.5, J=8.9 Hz, 1H), 4.68 (d, J=5.7 Hz, 1H), 4.74 (d, J=7.8 Hz, 1H), 4.91 (q, J=5.0 Hz, 1H), 5.13 (d, J=3.0 Hz, 1H), 5.26 (2xd, J=5.3, J=3.3 Hz, 1H), 5.28 (2xd, J=5.3, J=3.3 Hz, 1H), 5.98 (d, J=10.5 Hz, 2H), 6.40 (s, 2H), 6.58 (s, 1H), 7.00 (s, 1H).

$^{13}$C NMR (125 MHz, D$_2$O, δ): 22.13, 40.74, 43.56, 46.11, 59.12, 68.70, 70.41, 72.40, 75.46, 75.95, 76.95, 82.46, 94.87, 102.88, 103.66, 104.62, 111.14, 112.82, 113.23, 130.73, 135.45, 135.74, 140.22, 149.56, 151.43, 154.94, 166.36, 181.61.

$^{31}$P NMR (200 MHz, D2O, δ): s (2.19).

V. Synthesis of Phosphonooxymethylating Agents

Va. Synthesis of chloromethyldibenzyl phosphate

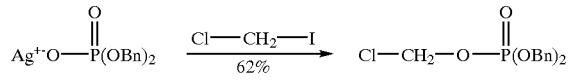

To a refluxed solution of chloroiodomethane (25 g of 97%, 0.14 mol) in toluene (HPLC-grade, 30 mL) was added silver dibenzylphosphate (7.0 g, 0.018 mol) in several portions over 20 minutes. Refluxing was continued for one hour. After the reaction mixture was cooled down to room temperature and filtered, the solvent was evaporated under reduced pressure. The oily residue was purified by silica gel flash column chromatography (7:3 hexane/ethyl acetate) to give 3.63 g (62% yield) of the title compound as a yellow oil.

FABMS+(NBA): [MH]$^+$, m/z 327

$^1$H NMR (300 MHz, CDCl$_3$, δ): 5.10 (d, J=8.0 Hz, 4H), 5.63 (d, J=15.7 Hz, 2H), 7.36 (s, 10H).

$^{13}$C NMR (75 MHz, CDCl$_3$, δ): 69.68, 69.75, 73.33, 73.42, 127.93, 128.51, 128.63, 135.07.

Vb. Synthesis of dibenzyl (p-toluenesulfonemethyl)-phosphate

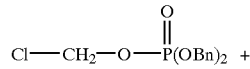

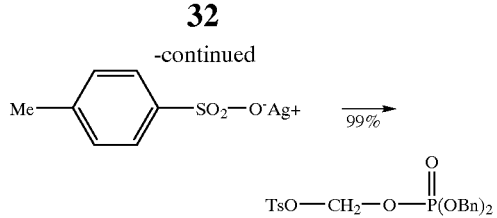

To a stirred solution of silver p-toluenesulfonate (600 mg, 2.15 mmol) in dry acetonitrile (3 mL) was added chloromethyl dibenzylphosphate (150 mg, 0.46 mmol) under an argon atmosphere. After the reaction mixture was stirred for 21 hours at room temperature, the solvent was removed, and the residue extracted with ether (3×3 mL). The combined extracts were filtered, evaporated, and dried in vacuo to give 210 mg (99% yield) of the title compound as a white solid.

EIMS: [MH]$^+$, m/z 463.

$^1$H NMR (300 MHz, CDCl$_3$, δ): 2.37 (s, 3H), 4.91 (2 ×d, J=7.9 Hz, 4H), 5.61 (d, J=14.2 Hz, 2H), 7.29 (m, 12H), 7.78 (d, J=8.4 Hz, 2H).

With respect to the above reaction Vb, as explained also in Ic above, the reagent:

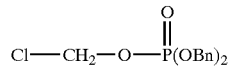

can be generically represented by the following formula:

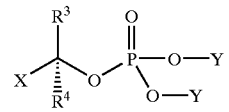

wherein all symbols are the same as defined above.

Vc. Synthesis of formaldehyde bis (dibenzyloxyphosphono)-acetal:

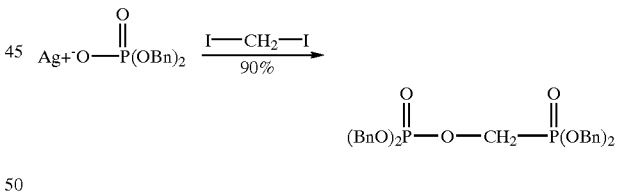

To a solution of diiodomethane (4 mL, 50 mmol) in dry toluene (15 mL) was added silver dibenzylphosphate (3.0 g, 7.8 mmol). The resulting mixture was refluxed for 15 minutes under an argon atmosphere. The mixture was then cooled down to room temperature and filtered. Then the solvent was evaporated in vacuo. The oily residue was purified by silica gel flash column chromatography (1:1 hexane/ethyl acetate and then ethyl acetate) to yield a yellowish oil which then crystallized to give 1.97 g (90% yield) of the title compound as a white solid, mp 39–42° C.

CIMS (NH3): [MH]+, m/z 569.

$^1$H NMR (300 MHz, CDC$_3$, δ): 5.03 (d, J=7.9 Hz, 8H), 5.49 (t, J=14.3 Hz, 2H), 7.30 (m, 20H).

$^{13}$C NMR (75 MHz, CDCl$_3$, δ): 69.54, 69.61, 86.48, 127.88, 128.48, 128.55, 135.10, 135.20.

VI-Synthesis of O-Phosphonooxymethylcyclosporin A

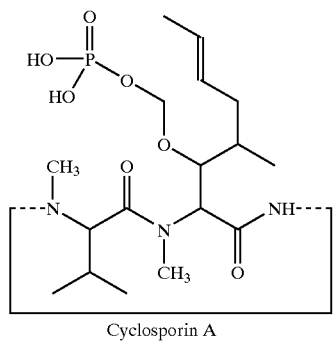

VIa. Synthesis of O-methylthiomethylcyclosporin A

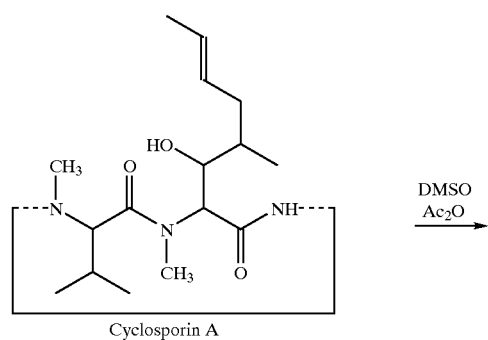

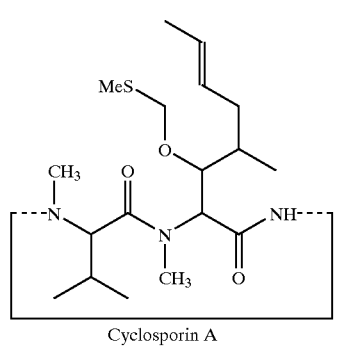

To a suspension of Cyclosporin A in dimethylsulfoxide (250 mL) is added acetic anhydride (125 mL) and acetic acid (35 mL). The heterogeneous mixture is vigorously stirred at room temperature for 24 hours, poured into ice (800 mL), stirred for 30 minutes, and then extracted with methylene chloride (4×100 mL). The combined methylene chloride extracts are washed with water (2×100 mL) and dried over magnesium sulfate. The methylene chloride is removed at reduced pressure to provide a product. The product is further purified by silica gel chromatography.

VIb. Synthesis of O-phosphonooxymethylcyclosporin A dibenzyl ester:

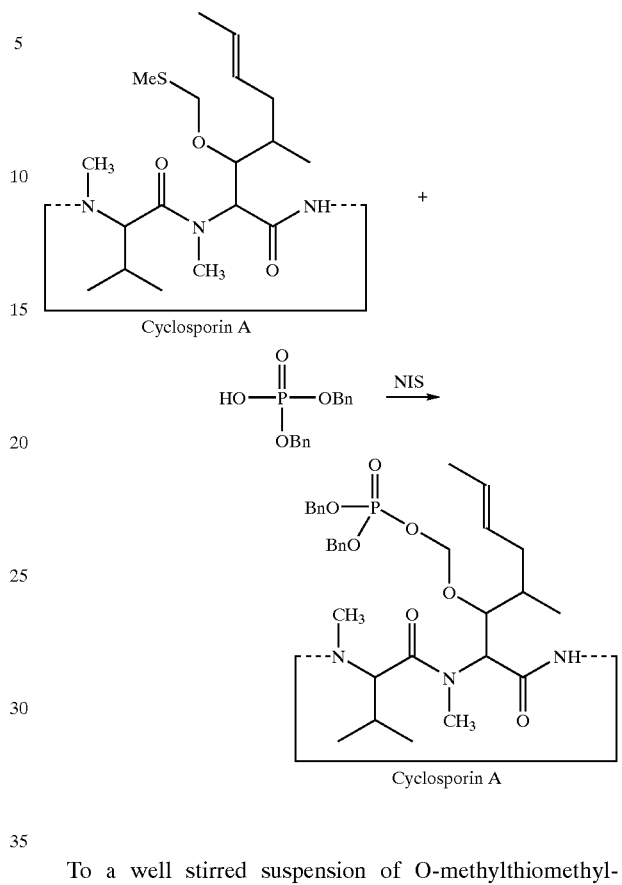

To a well stirred suspension of O-methylthiomethyl-cyclosporin A and powdered, activated 4 A molecular sieves (5 g) in tetrahydrofuran (20 mL) is added a suspension of N-iodosuccinimide (2.00 g of 95%, 8.44 mmol) and dibenzylphosphate (2.20 g, 7.83 mmol) in methylene chloride (12 mL). The resulting mixture is vigorously stirred at room temperature for 30 minutes, filtered, and diluted with ethyl acetate (300 mL). The solution is washed with aqueous sodium thiosulfate (10%, 2×15 mL), water (2×20 mL), brine (50 mL), and dried over magnesium sulfate. The mixture is filtered and the solvent is evaporated under reduced pressure. The residue is purified by silica gel flash column chromatography.

VIc. Synthesis of O-phosphonooxymethylcyclosporin A

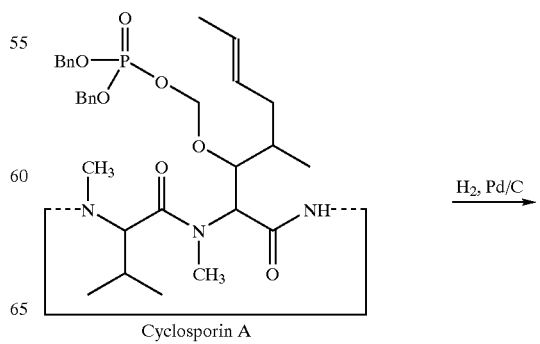

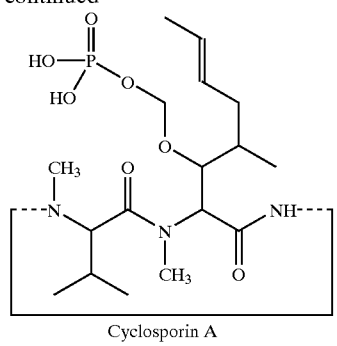

Cyclosporin A

To a solution of Q-phosphonooxymethylcyclosporin A dibenzyl ester in tetrahydrofuran (100 mL) and water (5 mL) is added palladium on carbon (10%, 500 mg). This mixture is stirred under an atmosphere of hydrogen (1 atm) for 35 minutes. The catalyst is removed by filtration through Celite. The Celite is then washed with tetrahydrofuran (300 mL) and the combined filtrates are evaporated at reduced pressure. The resulting solid is washed with ether (2×20 mL), hexane (50 mL), dried in vacuo, and then dissolved in hot methanol (60 mL). The solution is filtered, concentrated at reduced pressure to ~10 mL volume. After standing at room temperature for one hour, the solution is placed in a refrigerator overnight. The crystalline precipitate that forms overnight is filtered off and dried in vacuo to give the title compound as a solid. The filtrate is concentrated to ~1 mL volume and kept in the refrigerator for one hour to give additional product.

Biological Evaluation

Compounds of the present invention are novel pharmaceutical agents; representative compounds of formula I have been evaluated in in vitro and in vivo conversion studies. In all of these studies the prodrugs were converted into their pharmaceutically active parent compounds.

(1) Solubility Estimate of Propofol Prodrug in Water

The water solubility of propofol prodrug is approximately 500 mg/mL based on HPLC analysis of saturated aqueous solution.

(2) in vitro conversion of propofol prodrug to propofol

The in vitro conversion of propofol prodrug to propofol was performed using alkaline phosphatase in glycine buffer pH 10.4 medium. 25 mL of a 100 µg/mL propofol prodrug solution in glycine buffer was prepared. One millimeter was saved for a zero time point and the remaining 24 mL were placed in a 37° C. water bath. 960 µL of a 0.1 mg/mL alkaline phosphatase in glycine buffer solution was added to the 24 mL of propofol prodrug solution, mixed, and returned to the water bath. 1.5 mL samples were removed at 5, 10, 20, 30, 40, 60, 90, 120, 180, 240, 300, and 360 minutes. To each sample, 10 µL of glacial acetic acid was added immediately to stop the enzymatic reaction. The samples were assayed by HPLC to quantitate the propofol prodrug and propofol concentration. The results of the in vitro conversion are shown in FIG. 1. These results demonstrate that the propofol prodrug is a substrate for alkaline phosphatase.

(3) Gross Toxicity Evaluation in Rats

Propofol prodrug was prepared for i.v. injection at a concentration of 68 mg/mL in 0.9% Sodium Chloride Injection, USP. This concentration is equivalent to 36 mg/mL of propofol. The propofol prodrug solution was filtered through a 0.22 µm nylon membrane prior to administration.

The evaluation of the propofol prodrug on rats was conducted with two male Harlen Sprague-Dawley rats weighing 820 and 650 g. The 820 g rat received 200 µL of the propofol prodrug i.v. formulation (equivalent to 9 mg/kg of propofol) in the tail vein. A blood sample was taken from the tail vein (with heparinized syringe) after approximately 12 minutes. The 650 g rat received a dose of the mild sedative Metaphane® prior to receiving the propofol prodrug formulation. The 650 g rat was injected with 125 µL of the propofol prodrug formulation in the tail vein and a blood sample was taken from the tail vein (with heparinized syringe) after approximately six minutes. The blood samples from both rats were assayed for propofol by HPLC.

The results of the propofol prodrug injection in both rats were similar. Both rats became unsteady after a few minutes, but never lost their righting reflex. Based on visual observations, the rats fully recovered from the propofol prodrug injections. Blood removed from both rats confirmed the presence of propofol through HPLC analysis. The rats did not display signs of discomfort due to the propofol prodrug.

(4) Pharmacokinetic Evaluation in Dogs

A pharmacokinetic study involving Diprivan® or the propofol prodrug was performed in a dog with a sufficient washout period between studies. The blood concentrations were determined using HPLC with fluorescence detection while brain activity was monitored with two lead electroencephalography (EEG). Prior to dosing the dog, the dog was blindfolded, cotton was placed in the ears of the dog, and the legs of the dog were bound to minimize movement and other outside stimuli so that the effect of the propofol on the dog's brain wave activity could be most efficiently monitored.

The evaluation of the propofol blood concentration versus time was conducted with a beagle weighing ~13 kg. Approximately 8 mL of blood was taken prior to injection to be used for standard curve preparation and a zero time blood level. The dog received a volume of Diprivan® or propofol prodrug formulation equivalent to 7 mg/kg of propofol via injection in the cephalic vein.

Two mL blood samples were taken from either the cephalic (not the same vein as the formulation injection site), jugular, or saphenous vein (with heparinized syringe) after 1, 3, 5, 10, 15, 20 and 30 minutes after the injection. Blood samples were also taken after 60, 90, 120, 180, 240, 300, 360, 480, and 1440 minutes. Blood samples were extracted to remove the propofol immediately after being taken from the dog. The dog was fasted for approximately 20 hours prior to receiving the Diprivan® or propofol prodrug formulation. After the 120 minute sample was taken, the dog was allowed to drink water. Food was given to the dog after the 480 minute blood sample was obtained. The dog's regular diet was Hills' Science Diet Maintenance. The dog was on a light/dark cycle of 12 hours of light per day.

Figure 2:
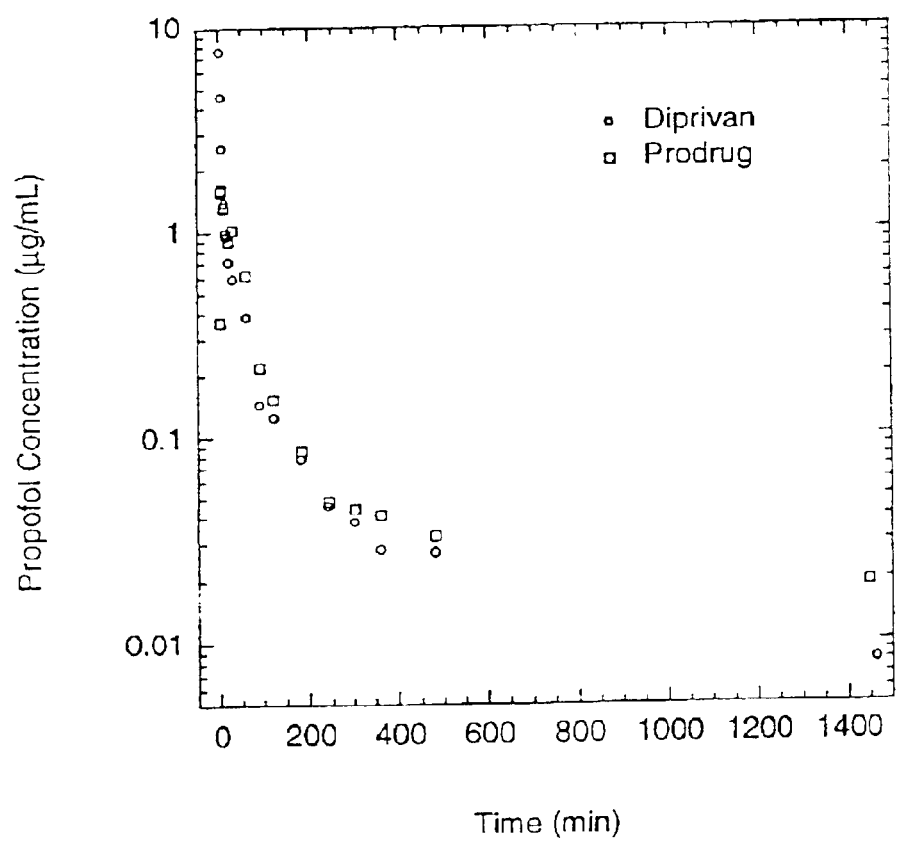
FIG. 2 illustrates the blood concentration change of propofol with respect to time from administration of the propofol prodrug or Diprivan® in a dog study.

The concentration of propofol in the blood samples was determined using HPLC with fluorescence detection. The results are shown in FIG. 2. The blood extraction and HPLC methods used were based on work reported by Plummer (1987) with minor modifications. The sample preparation and assay procedure used were as follows:

To a 1 mL sample of blood, 10 µL of thymol internal standard (20 µg/mL) and 1 mL phosphate buffer (0.1 M, pH 7.2) were added, vortexing to mix after each addition. Five mL of cyclohexane was then added and the samples were mixed at 75 rpm for 20–30 minutes. The organic layer was separated by 1 minute of centrifugation at approximately 2000 rmp. Approximately 4.5 mL of the organic layer was transferred to a tube containing 50 µL of dilute tetramethylammonium hydroxide (TMAH) solution at, approximately 1.8% (w/v). The solvent was evaporated to dryness under a stream of nitrogen and reconstituted with 200 µL of Mobile Phase A. The samples were centrifuged at 15,000 rmp for 30 seconds to remove any particles, and the supernatant was injected on the HPLC. Standard curve samples were prepared by spiking 1 mL aliquots of the initial blood with propofol at concentrations 5, 1, 0.5, 0.1 and 0.01 µg/mL. These standards were treated the same as the samples.

The HPLC system consisted of the following Shimadzu components: LC-10AT pumps, SCL-10A system controller, RF 353 fluorescence detector, and SIL-10A auto sampler. The HPLC parameters were as follows: excitation at 275 nm and emission at 320 nm; flow rate at 1 mL/min; injection volume was 3–30 µL depending on propofol concentration. The HPLC column was a Zorbax RX-C18, 15 cm×4.6 mm i.d., 5 µm particle size. Mobile Phase A was 60:40 (v/v) acetonitrile: 25 mM phosphate, 15 mM TBAP Buffer pH 7.1. Mobile Phase B was 80:10:10 (v/v/v) acetonitrile: water: THF. Mobile Phase B was used to clean the column after the thymol and propofol eluted using Mobile Phase A (4.2 and 7.4 minutes, respectively).

The dog exhibited signs of anesthesia upon injection of both formulations based on visual observations and EEG patterns. The dog recovered from anesthesia from both formulations in 20–30 minutes. Propofol blood levels resulting from injection of the propofol prodrug approximate those from injection of Diprivan®.

(5) Solubility Estimate of Camptothecin Prodrug in Water

The water solubility of the camptothecin prodrug is greater than 50 mg/mL based on visual and HPLC analysis.

(6) Camptothecin Prodrug (p-cpt) Enzymatic Study

A 16 µg/mL p-cpt was cleaved with acid phosphatase (0.02 units/mL of p-cpt solution). The media was 0.09 M citrate buffer, pH 4.8 and the temperature was 37° C. The conversion of p-cpt to camptothecin was monitored by HPLC.

Figure 3:
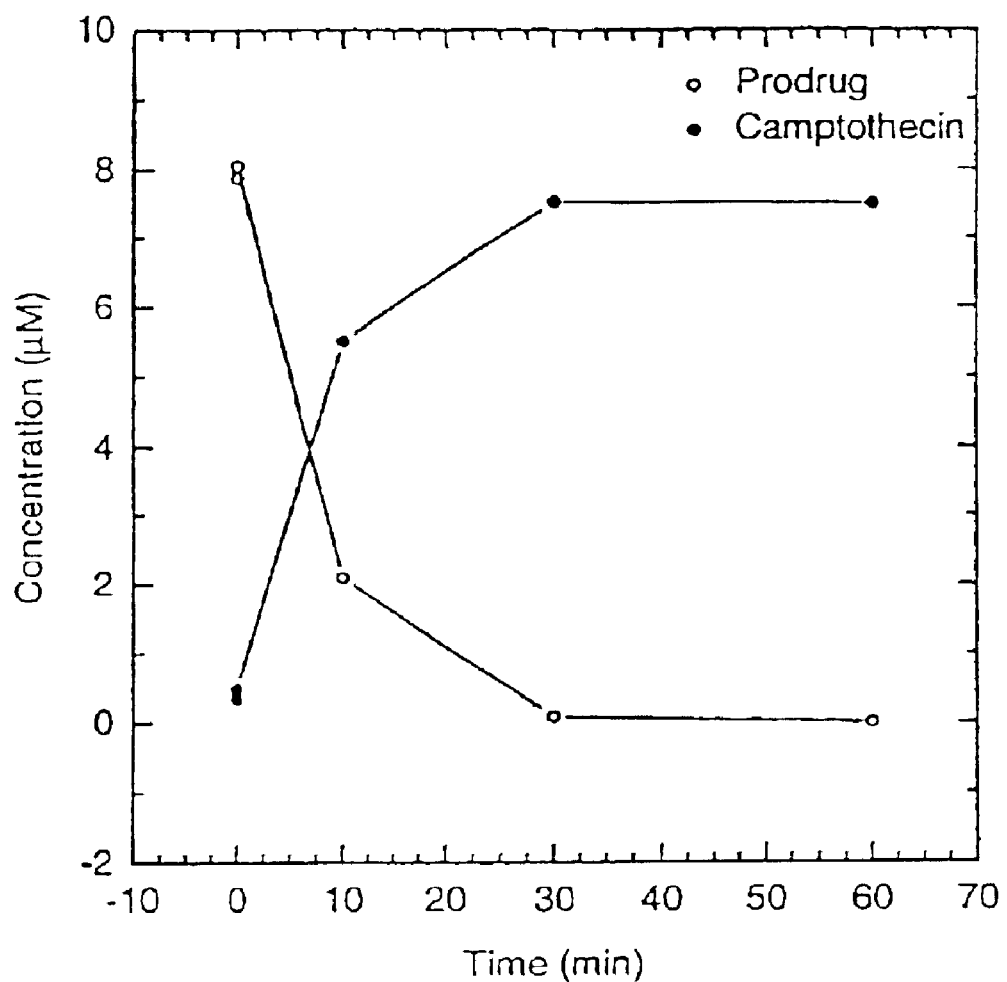
FIG. 3 illustrates an in vitro enzymatic conversion of camptothecin prodrug to camptothecin.

HPLC Parameters:
 MP: 24% potassium phosphate buffer pH 4, 76% acetonitrile
 Column: Zorbax RX-C18, 15 cm×4.6 mm i.d., 5 µm particle size
 Detection: 370 nm UV
 Flowrate: 1 mL/min Acid phosphatase from bovine prostate (sigma). The results are shown in FIG. 3. The results demonstrate that the camptothecin prodrug is a substrate for phophatases.

(7) Pharmacokinetic Study of the Camptothecin Prodrug Using Rats

Pharmacokinetic experiments involving the dosing of male Sprague-Dawley rats with formulations of the camptothecin prodrug and camptothecin were undertaken. The two formulations of the camptothecin prodrug that were examined consisted of the prodrug dissolved in 15 mM phosphate, pH 4.0 and camptothecin dissolved in organic co-solvents. The following is a summary of the pharmacokinetic experiments:

A volume of the camptothecin prodrug formulation or camptothecin formulation was prepared at a concentration so that a dose equivalent to 1 mg camptothecin per kg weight could be given to the rat. The formulation was given to the rat using an indwelling cannula in the left jugular vein of the rat. Blood samples were taken via an indwelling cannula located in the right jugular vein of the rat. Both cannulas were rinsed with heparinized saline prior to use and contained heparinized saline during the study.

The rats were anesthetized with sodium pentobarbital prior to insertion of the jugular cannulas and kept anesthetized with sodium pentobarbital during the study. The rats were placed on a 37° C. heating pad during the study and tracheotomized. Blood samples of approximately 150 µL were taken prior to dosing and after 1, 3, 5, 10, 15, 20, 30, 45, 60 and 90 minutes after the formulations were given to the rat.

The blood samples were placed in microcentrifuge tubes and centrifuged for 20 seconds at approximately 15000 rpm. A 50 µL aliquot of plasma from each blood sample was transferred to a second microcentrifuge tube. A 150 µL aliquot of chilled acetonitrile was added to the plasma and the preparation is vortexed for 5 seconds. A 450 µL aliquot of chilled sodium phosphate (0.1 M, pH 7.2) was then added. The contents in the microcentrifuge tubes were vortexed for 5 seconds and centrifuged for 20 seconds at approximately 15000 rpm. The supernatant was transferred to an HPLC autosampler set at 4° C. and analyzed (50 µL injections).

The HPLC system consisted of the following Shimadzu components: LC-10AT pump, SCL-10A system controller, RF 535 fluorescence detector, SIL-10A autosampler (set at 4° C.), and CTO-10A column oven (temperature set at 30° C.). The HPLC parameters were as follows: excitation at 370 nm and emission at 435 nm; flow rate at 2 mL/min. The HPLC column was a Hypersil ODS, 15 cm×4.5 mm i.d., 5 µm particle size. The mobile phase was 75% 25 nM sodium phosphate, pH 6.5/25% acetonitrile (v/v) with 25 mM tetrabutylammonium dihydrogen phosphate added as an ion-impairing reagent.

Figure 4:
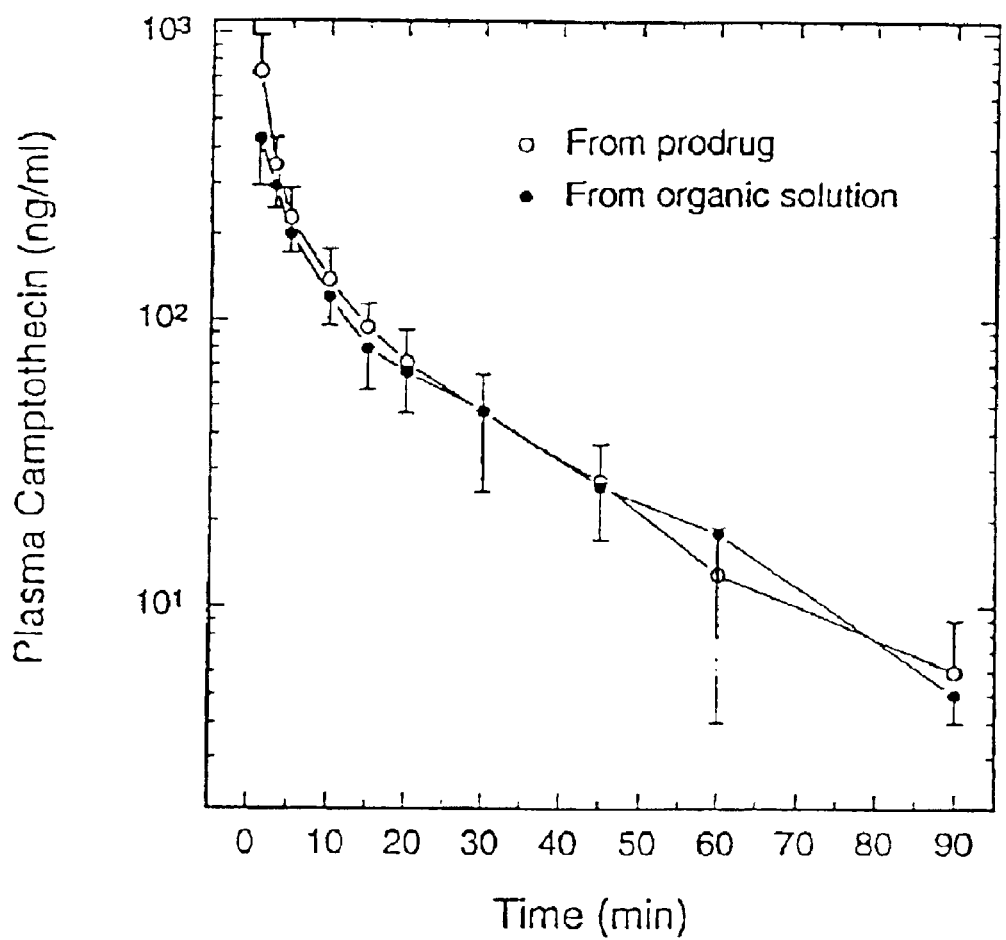
FIG. 4 illustrates the correlation between plasma concentration of camptothecin from the camptothecin prodrug and from camptothecin in organic co-solvents for a rat study.

As can be seen in the graph (FIG. 4) the prodrug provides camptothecin plasma levels which are equivalent to those attained from direct injection of camptothecin in organic co-solvents. The graph provides the mean with standard deviation for five rats which received prodrug and six rats which received camptothecin.

We claim:

1. A compound selected from the group consisting of O-phosphonoxymethylpropofol Dibenzy ester, O-phosphonoxymethyl-alpha-tocopherol Dibenzyl ester, and 4'-O-phosphonooxymethyletopside Dibenzyl ester.

2. A compound selected from the group consisting of O-phosphonoxymethylpropofol Disodium salt, O-phosphonoxymethyl-alpha-tocopherol Disodium salt, and 4'-O-phosphonoxymethyletoposide Disodium salt.

* * * * *